US011324733B2

(12) United States Patent
Maricich

(10) Patent No.: US 11,324,733 B2
(45) Date of Patent: *May 10, 2022

(54) METHODS FOR IMPROVING MEMORY AND COGNITION AND FOR TREATING MEMORY AND COGNITIVE DISORDERS

(71) Applicant: Cavion, Inc., Charlottesville, VA (US)

(72) Inventor: Yuri Maricich, Charlottesville, VA (US)

(73) Assignee: Cavion, Inc., Charlottesville, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/608,401

(22) PCT Filed: Apr. 26, 2018

(86) PCT No.: PCT/US2018/029616
§ 371 (c)(1),
(2) Date: Oct. 25, 2019

(87) PCT Pub. No.: WO2018/200850
PCT Pub. Date: Nov. 1, 2018

(65) Prior Publication Data
US 2020/0197377 A1    Jun. 25, 2020

Related U.S. Application Data

(60) Provisional application No. 62/490,377, filed on Apr. 26, 2017.

(51) Int. Cl.
*A61K 31/44* (2006.01)
*A61K 31/4439* (2006.01)
*A61K 31/4184* (2006.01)
*A61K 31/4418* (2006.01)
*A61K 31/554* (2006.01)
*A61K 31/713* (2006.01)
*A61P 25/28* (2006.01)
*A61K 45/06* (2006.01)
*C07D 213/65* (2006.01)
*C07D 207/08* (2006.01)
*C07D 235/14* (2006.01)
*C07D 239/82* (2006.01)
*C07K 16/28* (2006.01)

(52) U.S. Cl.
CPC .............. *A61K 31/44* (2013.01); *A61P 25/28* (2018.01); *A61K 45/06* (2013.01)

(58) Field of Classification Search
CPC .... A61K 31/44; A61K 45/06; A61K 31/4439; A61K 31/4184; A61K 31/554; A61K 31/4418; A61K 31/713; A61K 2039/505; A61P 25/28; C07D 213/65; C07D 235/14; C07D 239/82; C07D 207/08; C07K 16/28
See application file for complete search history.

(56) References Cited

U.S. PATENT DOCUMENTS

| | | |
|---|---|---|
| 4,808,605 A | 2/1989 | Branca et al. |
| 6,451,991 B1 | 9/2002 | Martin et al. |
| 7,112,319 B2 | 9/2006 | Broderick et al. |
| 7,319,098 B2 | 1/2008 | Cho et al. |
| 7,745,452 B2 | 6/2010 | Barrow |
| 7,875,636 B2 | 1/2011 | Barrow |
| 8,133,998 B2 | 3/2012 | Pajouhesh et al. |
| 8,263,627 B2 | 9/2012 | Barrow |
| 8,586,619 B2 | 11/2013 | Wu et al. |
| 8,637,513 B2 | 1/2014 | Barrow |
| 10,292,989 B2 | 5/2019 | Jevtovic-todorovic et al. |
| 2001/0049447 A1 | 12/2001 | Li et al. |
| 2003/0158143 A1 | 8/2003 | Gleave et al. |
| 2004/0198822 A1 | 10/2004 | Fraser |
| 2005/0245535 A1 | 11/2005 | Hangeland et al. |
| 2006/0003985 A1* | 1/2006 | Renger ................. A61K 31/455 514/211.07 |
| 2008/0293786 A1 | 11/2008 | Hahn et al. |
| 2009/0270413 A1 | 10/2009 | Galemmo, Jr. et al. |
| 2009/0325979 A1 | 12/2009 | Choi et al. |
| 2010/0004286 A1 | 1/2010 | Cho et al. |
| 2010/0056545 A1 | 3/2010 | Shin et al. |
| 2010/0094006 A1 | 4/2010 | Nam et al. |
| 2010/0137403 A1 | 6/2010 | Malstrom et al. |
| 2010/0151022 A9 | 6/2010 | Lenaerts |
| 2010/0216841 A1 | 8/2010 | Barrow et al. |
| 2014/0004186 A1 | 1/2014 | Hustvedt |
| 2014/0155444 A1 | 6/2014 | Tung et al. |

(Continued)

FOREIGN PATENT DOCUMENTS

| | | |
|---|---|---|
| CN | 102695506 A | 9/2012 |
| EP | 1568695 | 8/2005 |

(Continued)

OTHER PUBLICATIONS

Hanyu, H., "Nilvadipine prevents cognitive decline in patients with mild cognitive impairment." Intl J Geriatr Psychiatry 22 (2007): 1264-1266.*
Porter, V. R., "Frequency and characteristics of anxiety among patients with Alzheimer's disease and related dementias." The Journal of neuropsychiatry and clinical neurosciences 15.2 (2003): 180-186.*
Egan, M. F., "Randomized controlled study of the T-type calcium channel antagonist MK-8998 for the treatment of acute psychosis in patients with schizophrenia." Human Psychopharmacology: Clinical and Experimental 28.2 (2013): 124-133.*

(Continued)

*Primary Examiner* — John M Mauro
(74) *Attorney, Agent, or Firm* — Morrison & Foerster LLP

(57) ABSTRACT

This disclosure provides methods for the treatment of disease by administering pharmaceutical compounds. In particular, the disclosure relates to the treatment to improve memory or cognition, or to treat a memory or cognitive disorder, or to treat cognitive symptoms of a disease or condition by administering a T-type calcium channel antagonist.

10 Claims, 1 Drawing Sheet

(56) References Cited

U.S. PATENT DOCUMENTS

| | | | |
|---|---|---|---|
| 2018/0280357 A1 | 10/2018 | Maricich et al. | |
| 2020/0163943 A1 | 5/2020 | Maricich et al. | |

FOREIGN PATENT DOCUMENTS

| | | |
|---|---|---|
| EP | 1757590 | 2/2007 |
| EP | 2010493 B1 | 1/2016 |
| KR | 2009044924 | 5/2009 |
| KR | 101679262 | 11/2016 |
| WO | WO 1993004047 | 3/1993 |
| WO | WO 2004035000 | 4/2004 |
| WO | WO 2005007124 | 1/2005 |
| WO | WO 2005009392 | 2/2005 |
| WO | WO 2006023881 | 3/2006 |
| WO | WO 2006023883 | 3/2006 |
| WO | WO 2006098969 | 9/2006 |
| WO | WO 2007002361 | 1/2007 |
| WO | WO 2007002884 | 1/2007 |
| WO | WO 2007007852 | 1/2007 |
| WO | WO 2007073497 | 6/2007 |
| WO | WO 2007120729 | 10/2007 |
| WO | WO 2008007835 | 1/2008 |
| WO | WO 2008018655 | 2/2008 |
| WO | WO 2008033447 | 3/2008 |
| WO | WO 2008033456 | 3/2008 |
| WO | WO 2008033460 | 3/2008 |
| WO | WO 2008033464 | 3/2008 |
| WO | WO 2008033465 | 3/2008 |
| WO | WO 2008050200 | 5/2008 |
| WO | WO 2008110008 | 9/2008 |
| WO | WO 2008117148 | 10/2008 |
| WO | WO 2009009015 | 1/2009 |
| WO | WO 2009035307 | 3/2009 |
| WO | WO 2009054982 | 4/2009 |
| WO | WO 2009054983 | 4/2009 |
| WO | WO 2009054984 | 4/2009 |
| WO | WO 2009056934 | 5/2009 |
| WO | 2009133128 A1 | 11/2009 |
| WO | WO 2009146539 | 12/2009 |
| WO | WO 2009146540 | 12/2009 |
| WO | WO 2010083264 | 7/2010 |
| WO | WO 2010141842 | 12/2010 |
| WO | 2011093393 A1 | 8/2011 |
| WO | WO 2011019262 | 11/2011 |
| WO | WO 2012094615 | 7/2012 |
| WO | WO 2013169857 | 11/2013 |
| WO | WO 2014110409 | 7/2014 |
| WO | 2016203239 A1 | 12/2016 |
| WO | 2017044578 A1 | 3/2017 |
| WO | WO 2017070680 | 4/2017 |
| WO | 2018200844 A1 | 11/2018 |
| WO | 2018200850 A1 | 11/2018 |
| WO | 2019175395 A1 | 9/2019 |
| WO | 2020072773 A9 | 7/2020 |
| WO | 2021067697 A1 | 4/2021 |

OTHER PUBLICATIONS

Matsunaga, S., "Memantine monotherapy for Alzheimer's disease: a systematic review and meta-analysis." PloS one 10.4 (2015): e0123289.*

Bailus et al., "The prospect of molecular therapy for Angelman syndrome and other monogenic neurologic disorders," BMC Neurosci., Jun. 2014, 15:76.

Blom et al., "Preparative LC-MS Purification: Improved Compound Specific Method Optimization," J Comb. Chem., 2004, 6(6):874-883.

Bourinet et al., "Silencing of the Cav3.2 T-type calcium channel gene in sensory neurons demonstrates its major role in nociception," EMBO J., 2005, 24(2):315-324.

Carter et al., "Humanization of an anti-p185HER2 antibody for human cancer therapy," Proc. Natl. Acad. Sci. USA, May 1992, 89(10):4285-9.

Casillas-Espinosa et al., "Z944, a novel selective t-type calcium channel antagonist delays the progression of seizures in the amygdala kindling model," PLoS One, Aug. 14, 2015, 10(8):1-12.

Cech, "Ribozymes and their medical implications," JAMA, Nov. 1988, 260(20):3030-4.

Flatters, "T-type calcium channels: a potential target for the treatment of chronic pain," Drugs Future, 2005, 30(6):573-580.

Gadde et al., "Combination therapy of zonisamide and bupropion for weight reduction in obese women: a preliminary randomized, open-label study," Journal of Clinical Psychiatry, 68(8):1226-9, Aug. 2007.

Giordanetto et al., "T-type calcium channels inhibitors: a patent review," Expert Opin. Ther. Pat., Jan. 2011, 21(1):85-101.

Haselof et al., "Simple RNA enzymes with new and highly specific endoribonuclease activities," Nature, Aug. 1988, 334(6183):585-91.

Huang et al., "Topoisomerase inhibitors unsilenced the dormant allele of Ube3a in neurons," Nature, Jan. 2012, 481(7380):185-89.

Huguenard et al., "Intrathalamic rhythmicity studied in vitro: nominal T-current modulation causes robust antioscillatory effects," J Neuroscience, 1994, 14(9):5485-5502.

Jefferies et al., "A catalytic 13-mer ribozyme," Nucleic Acids Res., Feb. 1989, 17(4):1371-7.

Jones et al., "Replacing the complementarity-determining regions in a human antibody with those from a mouse," Nature, May-Jun. 1986, 321(6069):522-25.

Kim et al., "Three-dimensional model of the active site of the self-splicing rRNA precursor of Tetrahymena," Proc. Natl. Acad. Sci. USA, Dec. 1987, 84(24):8788-92.

McGivern, "Targeting N-type and T-type calcium channels for the treatment of pain," Drug Discovery Today, 2006, 11(5-6):245-53.

Miller et al., "Mapping genetic modifiers of survival in a mouse model of Dravet syndrome," Genes Brain Behav., Feb. 2014, 13(2):163-172.

Nolt et al., "Assessment of anticonvulsant effectiveness and safety in patients with Angelman's syndrome using an Internet questionnaire," American journal of health-system pharmacy, Dec. 2003, 60(24):2583-7.

Pasek et al., "Differential CaMKII regulation by voltage-gated calcium channels in the striatum," Mol. Cell. Neurosci., Sep. 2015, 68:234-43.

PCT International Preliminary Report on Patentability in International Appln. No. PCT/US2018/29616, dated Oct. 29, 2019, 7 pages.

PCT International Preliminary Report on Patentability in International Appln. No. PCT/US2018/029610, dated Oct. 29, 2019, 5 pages.

PCT International Preliminary Report on Patentability in International Appln. No. PCT/US2016/058487, dated May 3, 2018, 7 pages.

PCT International Search Report and Written Opinion in International Appln. No. PCT/US2018/18356, dated May 8, 2018, 9 pages.

PCT International Search Report and Written Opinion in International Appln. No. PCT/US2018/29616, dated Jul. 11, 2018, 7 pages.

PCT International Search Report and Written Opinion in International Appln. No. PCT/US2016/058487, dated Jan. 3, 2017, 27 pages.

PCT Internationl Search Report and Written Opinion in International Appln. No. PCT/US2018/29610, dated Jul. 19, 2018, 7 pages.

Peturssion et al., "Protecting Groups in Carbohydrate Chemistry," J Chem. Educ., 1997, 74(11):1297-1303.

Powell et al., "Low threshold T-type calcium channels as targets for novel epilepsy treatments," British Journal of Clinical Pharmacology, Jul. 2013, 77(5):729-739.

PUBCHEM-CID 57173592, dated Jun. 14, 2012.

Radin et al., "Treatment of Obese Female and Male SHHF/Mcc-facp Rats with Antihypertensive Drugs, Nifedipine and Enalapril: Effects on Body Weight, Fat Distribution, Insulin Resistance and Systolic Pressure," Obesity research, Nov. 1993, 1(6):433-442.

Riechmann et al., "Reshaping human antibodies for therapy," Nature, Mar. 1988, 332(6162):323-27.

Silva-Santos et al., "Ube3a reinstatement identifies distinct developmental windows in a murine Angelman syndrome model," J. Clin. Invest., May 2015, 125(5):2069-2076.

(56) References Cited

OTHER PUBLICATIONS

Sims et al., "A humanized CD18 antibody can block function without cell destruction," J. Immunol., Aug. 1993, 151(4):2296-308.

Still et al., "Rapid chromatoeraphic technique for preparative separations with moderate resolution," J Org. Chem., 1978, 43(14):2923-2925.

Verhoeven et al., "Reshaping human antibodies: grafting an antilysozyme activity," Science, Mar. 1988, 239(4847):1534-36.

Yamauchi et al., "Neuronal Ca2+/calmodulin-dependent protein kinase II—discovery, progress in a quarter of a century, and perspective: implication for learning and memory," Biological and Pharmaceutical Bulletin, May 2005, 28(8):1342-1354.

Ashford, S. et al. (2006), "Goal Attainment for Spasticity Management Using Botulinum Toxin," Physiotherapy Research International 11(1):24-34.

Bain, P.G. et al. (1993). "Assessing Tremor Severity," Journal of Neurology, Neurosurgery & Psychiatry 56(8):868-873.

Bermejo-Pareja, F. (2011, e-pub Apr. 12, 2011). "Essential Tremor—A Neurodegenerative Disorder Associated With Cognitive Defects?" Nature Reviews Neurology 7(5):273-282.

Bermejo-Pareja, F.et al. (Sep. 14, 2012). "Cognitive Features of Essential Tremor: A Review of the Clinical Aspects and Possible Mechanistic Underpinnings," Tremor and Other Hyperkinetic Movements 2:13 pages.

Bezençon, O. et al. (2017). "Milestones to the Discovery of T-Type Calcium Channel Blockers for the Treatment of Generalized Epilepsies," CHIMIA International Journal for Chemistry 71(10):722-729.

Chandran, V. et al. (2012). "Non-Motor Features in Essential Tremor," Acta Neurologica Scandinavica 125(5):332-337.

clinicaltrials.gov (Apr. 5, 2017). "A Phase 2 RCT Study of CX-8998 for Essential Tremor," clinicaltrials.gov No. NCT03101241, 8 pages, retrieved from https://clinicaltrials.gov/ct2/show/NCT03101241.

Cribbs, L.L. et al. (Jul. 13, 1998). "Cloning and Characterization of Alpha1h From Human Heart, a Member of the T-Type Ca2+ Channel Gene Family," Circulation Research 83(1):103-109.

Elbe, R. et al. (2013, e-pub Sep. 3, 2013). "Task Force Report: Scales for Screening and Evaluating Tremor: Critique and Recommendations," Movement Disorders 28(13):1793-1800.

Elble, R. et al. (Jun. 26, 2008). "1094 The Essential Tremor Rating Assessment Scale (TETRAS)," Mov Disord. 23 (Suppl 1):S357.

Elble, R. et al. (Oct. 2012). "Reliability of a New Scale for Essential Tremor," Movement Disorders 27(12):1567-1569.

Elble, R.J. et al. (Jan. 1996). "Quantification of Essential Tremor in Writing and Drawing," Movement Disorders: Official Journal of the Movement Disorder Society 11(1):70-78.

Ertel, E.A. et al. (Mar. 2000). "Nomenclature of Voltage-Gated Calcium Channels," Neuron 25(3):533-535.

Fahn, S. et al. (1987). Recent Developments in Parkinson's Disease 2:153-163 and 293-304, 8 pages, as retrieved or May 21, 2021 from https://www.parkinsons.va.gov/resources/UPDRS.asp.

Fahn, S. et al. (1988). "Clinical Rating Scale for Tremor," Parkinson's Disease and Movement Disorders 2:225-234.

George, M.S. et al. (Dec. 1994). "Social Phobia Secondary to Physical Disability: A Review of Benign Essential Tremor (BET) and Stuttering," Psychosomatics 35(6):520-523, 7 pages.

Handforth, A. et al. (2005). "Pharmacologic Evidence for Abnormal Thalamocortical Functioning in GABAA Receptor β3 Subunit-Deficient Mice, a Model of Angelman Syndrome," Epilepsia 46(12):1860-1870.

Haubenberger, D. et al. (Sep. 2016). "Transducer-Based Evaluation of Tremor," Movement Disorders 31(9):1327-1336, 21 pages.

Hoffman, J.D. et al. (Aug. 30, 2011). "Objective Measure of Upper Extremity Motor Impairment in Parkinson's Disease With Inertial Sensors," Conf Proc IEEE Eng Med Biol Soc., 4378-4381.

Jannetti, P. et al. (Jul. 1, 2009, e-pub. Mar. 2009). Addition of Verapamil in the Treatment of Severe Myoclonic Epilepsy in Infancy, Epilepsy Research 85(1):89-95.

Iftinca, M.C. et al. (2009). "Regulation of Neuronal T-Type Calcium Channels," Trends in Pharmacological Sciences 30(1):32-40.

Iinuma, K. et al. (Dec. 1, 2004). "Clinical Efficacy of Zonisamide in Childhood Epilepsy After Long-Term Treatment: A Postmarketing, Multi-Institutional Survey", Seizure GB, 13:534-539.

International Search Report and Written Opinion of the Searching Authority dated Dec. 10, 2019, for Patent Application No. PCT/US2019/054498, 13 pages.

International Search Report and Written Opinion of the Searching Authority dated Jan. 3, 2017, for Patent Application No. PCT/US2016/058487, filed Oct. 24, 2016, 8 pages.

International Search Report and Written Opinion of the Searching Authority dated Jan. 13, 2021, for Patent Application No. PCT/US2020/053944, 8 pages.

Jiang, Y.-H., et al. (Oct. 1998). "Mutation of the Angelman Ubiquitin Ligase in Mice Causes Increased Cytoplasmic P53 and Deficits of Contextual Learning and Long-Term Potentiation," Neuron 21(4):799-811.

Jinnah, H. et al. (2020). "Efficacy and Safety of CX-8998 in T-CALM, a Randomized, Double-Blind, Placebo-Controlled, Phase 2a Trial in Participants With Essential Tremor: Subgroup Analysis by Baseline Tremor Severity," International Parkinson and Movement Disorder Society, Virtual Congress 2020, Sep. 12-14, 2020, 1 page.

Jinnah, H.A. et al. (2020). "Efficacy and Safety of CX-8998 in T-CALM, a Randomized, Double-Blind, Placebo-Controlled, Phase 2a Trial in Participants With Essential Tremor: Subgroup Analysis by Baseline Tremor Severity," Virtual presentation presented at American Academy of Neurology, May 18, 2020, 12 pages.

Jinnah, H.A. et al. (Apr. 14, 2020). "Efficacy and Safety of CX-8998 in T-CALM, a Randomized, Double-Blind, Placebo-Controlled, Phase 2a Trial in Participants With Essential Tremor: Subgroup Analysis by Baseline Tremor Severity (1842)," Neurology 94 (Suppl 15), 7 pages, Abstract Only.

Jinnah, H.A. et al. (Sep. 2020). "Efficacy and Safety of CX-8998 in T-CALM, a Randomized, Double-Blind, Placebo-Controlled, Phase 2a Trial in Participants With Essential Tremor: Subgroup Analysis by Baseline Tremor Severity. [MDS 2020 Abstract 1474]," Mov Disord. 35 (Suppl 1):S687, 3 pages.

Kamper, S.J. et al. (2009). "Global Rating of Change Scales: A Review of Strengths and Weaknesses and Considerations for Design," Journal of Manual & Manipulative Therapy 17(3):163-170.

Keened, L. et al. (1989). "Flunarizine as a Supplementary Medication in Refractory Childhood Epilepsy a Double-Blind Crossover Study", Canadian Journal of Neurological Sciences 16(2):191-193.

Khan, F. et al. (Apr. 2008). "Use of Goal Attainment Scaling in Inpatient Rehabilitation for Persons With Multiple Sclerosis," Archives of Physical Medicine and Rehabilitation 89(4):652-659.

Kiresuk, T.J. et al. (1968). "Goal Attainment Scaling: A General Method for Evaluating Comprehensive Community Mental Health Programs," Community Mental Health Journal 4(6):443-453.

Lee, J,-H. et al. (Mar. 15, 1999). "Cloning and Expression of a Novel Member of the Low Voltage-Activated T-Type Calcium Channel Family," Journal of Neuroscience 19(6):1912-1921.

Lee, M. (2019). "The Biology of Pathological Oscillations in the Brain: Potential Novel Targets for Tremor Disorders," International Congress of Parkinson's Disease and Movement Disorders, Nice, France, Sep. 22-26, 2019, 21 pages.

Lee, M. et al. (Apr. 9, 2018). Reversal of Allodynia and Neurophysiological Outcomes by CX-8998, a Potent, 1-3 Selective T-Type Calcium Channel Modulator, in a Model of Bortezomib Induced Peripheral Neurotoxicity (S7.004), Neurology 90:6 pages (Abstract Only).

Lee, M.S. et al. (2018). "Therapeutic Exposures of CX-8998, a Potent, Selective and State Dependent T-type Calcium Channel (Cav3) Antagonist with Dose Dependent Efficacy in Cav3 Driven Neurological Models," Mov Disord. 33(suppl 2):S10, Poster presented at International Congress of the Parkinson and Movement Disorder Society, Oct. 5-9, 2018, Hong Kong.

Lee, M.S. et al. (2018). "Therapeutic Exposures of CX-8998, a Potent, Selective Cav3 Channel Antagonist With Dose Dependent Efficacy in Cav3 Driven Neurological Models," Neurotherapeutics

(56) References Cited

OTHER PUBLICATIONS

15:830, Poster #31 presented at American Society for Experimental Neurotherapeutics, Mar. 7-10, 2018, Rockville, MD.

Llinás, R.R. (2003). "Thalamo-Cortical Dysrhythmia Syndrome: Neuropsychiatric Features," An R Acad Nac Med (Madr). 120(2):267-290, 52 pages, English Translation.

Llinás, R.R. et al. (2007). "γ-Band Deficiency and Abnormal Thalamocortical Activity in P/Q-Type Channel Mutant Mice," Proceedings of the National Academy of Sciences 104(45):17819-17824.

Long, M.A. et al. (2002). "Rhythmicity Without Synchrony in the Electrically Uncoupled Inferior Olive," Journal of Neuroscience 22(24):10898-10905.

Lopez, S.J. et al. (Jan. 4, 2019). "UBE3A: An E3 Ubiquitin Ligase With Genome-Wide Impact in Neurodevelopmental Disease," Frontiers in Molecular Neuroscience vol. 11, Article No. 476, pp. 1-8.

Lorenz, D. et al. (2006). "Quality of Life and Personality in Essential Tremor Patients," Movement Disorders: Official Journal of the Movement Disorder Society 21(8):1114-1118.

Louis, E.D. (Oct. 2000). "Essential Tremor," Arch Neurol. 57(10): 1522-1524, 5 pages.

Louis, E.D. et al. (1998). "How Common is the Most Common Adult Movement Disorder? Estimates of the Prevalence of Essential Tremor Throughout the World," Movement Disorders: Official Journal of the Movement Disorder Society 13(1):5-10.

Louis, E.D. et al. (2010). "How Common is the Most Common Adult Movement Disorder? Update on the Worldwide Prevalence of Essential Tremor," Movement Disorders 25(5):534-541.

Louis, E.D. et al. (2015). "Tremor-Related Quality of Life: A Comparison of Essential Tremor Vs. Parkinson's Disease Patients." Parkinsonism & Related Disorders 21(7):729-735.

Maricich, Y. et al. (2017). "TETRAS Applicability and Study Design in Randomized, Placebo Controlled Clinical Evaluation of Cav3 modulation for patients with essential tremor," Mov Disord. 32(suppl 2):S296, Poster presented at International Congress of the Parkinson and Movement Disorder Society, Jun. 4-8, 2017, Vancouver, BC, Canada.

Mitsi, G. et al. (Jun. 13, 2017). "Biometric Digital Health Technology for Measuring Motor Function in Parkinson's Disease: Results From a Feasibility and Patient Satisfaction Study," Frontiers in Neurology 8:273, 5 pages.

Molineux, M.L. et al. (Apr. 4, 2006). "Specific T-Type Calcium Channel Isoforms Are Associated With Distinct Burst Phenotypes in Deep Cerebellar Nuclear Neurons," Proc Natl Acad Sci USA 103(14):5555-5560.

Mostile, G. et al. (2010). "Correlation Between Kinesia System Assessments and Clinical Tremor Scores in Patients With Essential Tremor," Movement Disorders 25(12):1938-1943.

Nicoll, R.A. (Jan. 18, 2017). "A Brief History of Long-Term Potentiation," Neuron 93(2):281-290.

Ondo W. et al. (2020). "Efficacy and Safety of the T-Type Calcium Channel Modulator CX-8998 in T-CALM, a Randomized, Double-Blind, Placebo-Controlled, Phase 2a Trial in Participants with Essential Tremor," Annals of Neurology. vol. 88. 111 River St, Hoboken 07030-5774, NJ USA: 3 pages.

Ondo, W. et al. (2020). "Efficacy and Safety of the T-Type Calcium Channel Modulator CX-8998 in T-CALM, a Randomized, Double-Blind, Placebo-Controlled, Phase 2a Trial in Participants With Essential Tremor," Annual Meeting of the American Neurological Association, Virtual Meeting, Oct. 4-9, 2020, 1 page.

Papapetropoulos, S. et al. (2008). "A Questionnaire-Based (UM-PDHQ) Study of Hallucinations in Parkinson's Disease," BMC Neurology 8(1):1-8.

Papapetropoulos, S. et al. (2018). "A Novel, State-dependent Cav3 Channel Antagonist in Phase 2 Development for Tremor and Epilepsy," Neurotherapeutics 15:832, Poster presented at American Society for Experimental Neurotherapeutics, Mar. 7-10, 2018, Rockville, MD, 819-835.

Papapetropoulos, S. et al. (2018). "A Proof-of-Principle Quantitative EEG Study of an Oral, Potent and Selective T-Type Calcium Modulator in Healthy Volunteers," 90(suppl 15):P4.261, Poster presented at American Academy of Neurology; Apr. 21-27, 2018, Los Angeles, CA, 6 pages.

Papapetropoulos, S. et al. (2018). "Proof-of-Principle Quantitative EEG Study of CX-8998, an Oral, Potent and Selective T-Type Calcium Antagonist in Development for Symptomatic Treatment of Essential Tremor and Parkinson's Disease Tremor," Mov Disord. 33(suppl 2):S22, Poster presented at International Congress of the Parkinson and Movement Disorder Society, Oct. 5-9, 2018, Hong Kong.

Papapetropoulos, S. et al. (2019). "Efficacy Results From a Phase 2, Double-Blind, Placebo-Controlled Study of CX-8998 a State-Dependent T-Type Calcium (Cav3) Channel Modulator in Essential Tremor Patients (T-CALM)," American Academy of Neurology, Philadelphia, PA, May 4-10, 2019, 16 pages.

Papapetropoulos, S. et al. (Jun. 11, 2019). "A Phase 2, Randomized, Double-Blind, Placebo-Controlled Trial of CX-8998, a Selective Modulator of the T-Type Calcium Channel in Inadequately Treated Moderate to Severe Essential Tremor: T-CALM Study Design and Methodology for Efficacy Endpoint and Digital Biomarker Selection," Frontiers in Neurology 10:597, 11 pages.

Papapetropoulos, S. et al. (Mar. 25, 2021). "A Phase 2 Proof-of-Concept, Randomized, Placebo-Controlled Trial of CX-8998 in Essential Tremor," Mov Disord., 8 pages.

Papapetropoulos, S. et al. (May 5, 2019). "Efficacy results from a phase 2, double-blind, placebo-controlled study of CX-8998 a state-dependent T-type calcium (Cav3) channel modulator in essential tremor patients (T-CALM)," Neurology 92(suppl 15):S4.008, presented at American Academy of Neurology, Philadelphia, PA, May 4-10, 2019, 7 pages.

Park, Y-G. et al. (2010). "Cav3. 1 is a Tremor Rhythm Pacemaker in the Inferior Olive," Proceedings of the National Academy of Sciences 107(23):10731-10736.

Park, Y-G. et al. (2013)."The Potential Roles of T-Type Ca2+ Channels in Motor Coordination," Frontiers in Neural Circuits 7:172, 11 pages.

Perez-Reyes, E. (1998). "Molecular Characterization of a Novel Family of Low Voltage-Activated, T-Type, Calcium Channels," Journal of Bioenergetics and Biomembranes 30(4):313-318.

Pulliam, C.L. et al. (2014). "Continuous in-Home Monitoring of Essential Tremor," Parkinsonism & Related Disorders 20(1):37-40.

Reger, T.S. et al. (2011, e-pub Jan. 26, 2011) "Pyridyl Amides as Potent Inhibitors of T-Type Calcium Channels." Bioorganic & Medicinal Chemistry Letters 21(6):1692-1696.

Siegrist, R. et al. (2016). "Structure-Activity Relationship, Drug Metabolism and Pharmacokinetics Properties Optimization, and In Vivo Studies of New Brain Penetrant Triple T-Type Calcium Channel Blockers." Journal of Medicinal Chemistry 59(23):10661-10675.

So-Hee, E. et al. (Apr. 1, 2011). "Comparative Trial of Low- and High-Dose Zonisamide as Monotherapy for Childhood Epilepsy", Seizure 20(7):558-563.

Tröster, A.I. et al. (2005). "Quality of Life in Essential Tremor Questionnaire (QUEST): Development and Initial Validation." Parkinsonism & Related Disorders 11(6):367-373.

U.S. Appl. No. 17/282,730, Lee et al., filed Apr. 2, 2021 (Copy not submitted herewith pursuant to the waiver of 37 C.F.R. § 1 98(a)(2)(iii) issued by the Office on Sep. 21, 2004).

Voller, B. et al. (Apr. 2014). "Alcohol Challenge and Sensitivity to Change of the Essential Tremor Rating Assessment Scale," Movement Disorders 29(4): 555-558, 10 pages.

Xiang, Z. et al. (Dec. 21, 2011, e-pub Oct. 17, 2011). "The Discovery and Characterization of ML218: A Novel, Centrally Active T-Type Calcium Channel Inhibitor with Robust Effect in STN Neurons and in a Rodent Model of Parkinson's Disease," ACS Chemical Neuroscience 2(12):730-742.

Yağmur, I, et al. (May 28, 2016)."Benign Prostatic Hyperplasia: Case Report of a 17-Year-Old," Journal of Pediatric Urology 12(4):267-e1, 8 pages. (Abstract Only).

Zamponi, G.W. et al. (2015). "The Physiology, Pathology, and Pharmacology of Voltage-Gated Calcium Channels and Their Future Therapeutic Potential," Pharmacological Reviews 67(4):821-870.

(56) References Cited

OTHER PUBLICATIONS

Zesiewicz, T.A. et al. (2011). "Evidence-Based Guideline Update: Treatment of Essential Tremor: Report of the Quality Standards Subcommittee of the American Academy of Neurology," Neurology 77(19):1752-1755.

Zadionchenko, V.S. (2015). "Use of Calcium Channel Blockers in Patients With Cardiovascular Pathology: Focus on Diltiazem," Consilium Medicum 17(5):54-63, (English Translation of the Abstract).

Miwa, H. et al. (2011, e-pub. Apr. 12, 2011). "Type Calcium Channel as a New Therapeutic Target for Tremor," Cerebellum 10(3):563-569.

Nicita, F. et al. (2014). "Efficacy of Verapamil as an Adjunctive Treatment in Children With Drug-Resistant Epilepsy a Pilot Study," Seizure 23(1):36-40.

Plosker, G.L. (2012, e-pub. Sep. 26, 2012). "Stiripentol : In Severe Myoclonic Epilepsy of Infancy (Dravet Syndrome),"CNS Drugs 26(11):993-1001.

U.S. Appl. No. 17/591,498, Maricich et al., filed Feb. 2, 2022. (Copy not submitted herewith pursuant to the waiver of 37 C.F.R. § 1.98(a)(2)(iii) issued by the Office on Sep. 21, 2004).

* cited by examiner

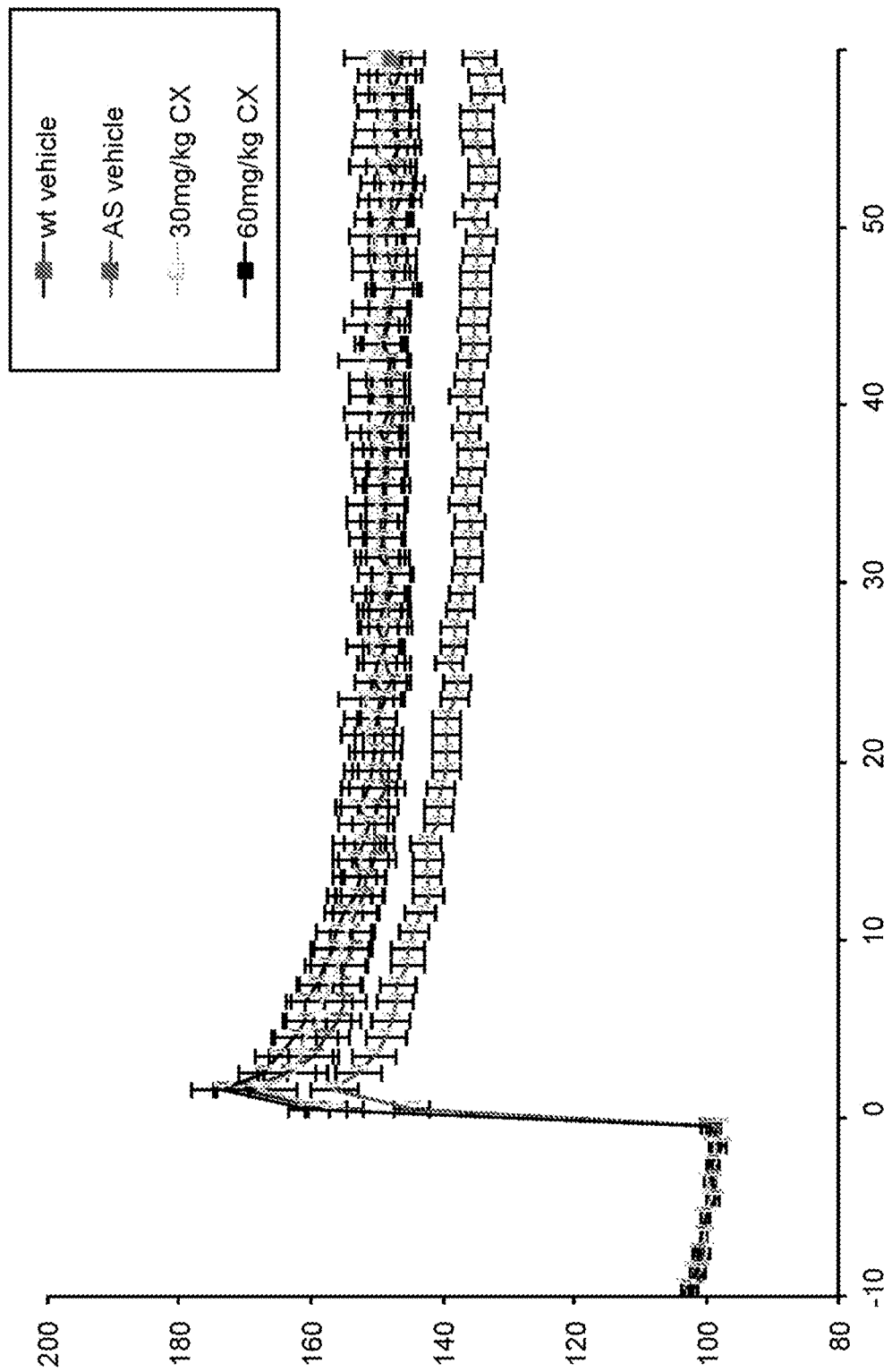

METHODS FOR IMPROVING MEMORY AND COGNITION AND FOR TREATING MEMORY AND COGNITIVE DISORDERS

CROSS-REFERENCE TO RELATED APPLICATIONS

This application is a national phase application under 35 U.S.C. § 371 of PCT International Application number PCT/US2018/029616, filed Apr. 26, 2018, which claims the benefit of U.S. Patent Application Ser. No. 62/490,377, filed on Apr. 26, 2017, the entire disclosures of which are incorporated herein in their entirety.

TECHNICAL FIELD

This disclosure relates to treatment of disease by administering pharmaceutical compounds. In particular, the disclosure relates to the treatment to improve memory or cognition, or to treat a memory or cognitive disorder, or to treat cognitive symptoms of a disease or condition by administering a T-type calcium channel antagonist.

BACKGROUND

T-type calcium channels are low-voltage activated calcium channels that open during membrane depolarization and mediate calcium influx into cells after an action potential or depolarizing signal. T-type calcium channels known to be present within cardiac and smooth muscle, and also are present in many neuronal cells within the central nervous system. T-type calcium channels (transient opening calcium channels) are distinct from L-type calcium channels (Long-Lasting calcium channels) due to their ability to be activated by more negative membrane potentials, their small single channel conductance, and their non-responsiveness to traditional calcium channel antagonist drugs, targeting L-type calcium channels.

T-type calcium channels open following small membrane depolarizations. T-type calcium channels have been primarily studied in the context of neuronal and cardiomyocyte function, and have been implicated in hyperexcitability disorders, such as epilepsy and cardiac dysfunction. Voltage gated calcium channels are not generally expressed in non-excitable cells, but there is evidence that T-type calcium channels are expressed in cancer cells of non-excitable lineages.

T-type calcium channels are activated and inactivated by small membrane depolarizations, and display slow deactivation rates. Thus, these channels can carry depolarizing current at low membrane potentials and mediate cellular "window" currents, which occur within the voltage overlap between activation and steady state inactivation at low or resting membrane potentials. T-type calcium channels can maintain window current at non-stimulated or resting membrane potentials, thereby allowing a sustained inward calcium current carried by a portion of channels that are not inactivated. Mediation of window current allows T-type calcium channels to regulate intracellular calcium levels, both in electrically firing cells such as neurons, and in non-excitable tissues, under non-stimulated or resting cellular conditions.

Voltage-gated calcium channels are made up of several subunits. The $\alpha_1$ subunit is the primary subunit that forms the transmembrane pore of the channel. The $\alpha_1$ subunit also determines the type of calcium channel. The $\beta$, $\alpha_2\delta$, and $\gamma$ subunits, present in only some types of calcium channels, are auxiliary subunits that play secondary roles in the channel. The $\alpha_1$ subunit is composed of four domains (I-IV), with each domain containing 6 transmembrane segments (S1-S6), and hydrophobic loops between the S5 and S6 segments of each domain form the pore of the channel. Sub-types of the T-type calcium channel are defined by the specific $\alpha_1$ subunit as shown in Table 1.

TABLE 1

| T-type Calcium Channel Sub-Types | | |
|---|---|---|
| Designation | $\alpha_1$ subunit | Gene |
| Cav3.1 | $\alpha_1$G | CACNA1G |
| Cav3.2 | $\alpha_1$H | CACNA1H |
| Cav3.3 | $\alpha_1$I | CACNA1I |

Cognition is the mental action or process of acquiring knowledge and understanding through thought, experience, and the senses. It encompasses processes such as knowledge, attention, memory and working memory, judgment and evaluation, reasoning and computation, problem solving and decision making, comprehension and production of language. In psychology the term is used to apply to processes such as memory, association, concept formation, pattern recognition, language, attention, perception, action, problem solving and mental imagery. Neurocognitive functions are cognitive functions closely linked to the function of particular areas, neural pathways, or cortical networks in the brain substrate layers of neurological matrix at the cellular molecular level. Cognition is severely damaged in dementia.

Memory is the faculty of the mind by which information is encoded, stored, and retrieved. Short-term memory is the capacity for holding, but not manipulating, a small amount of information in mind in an active, readily available state for a short period of time. Working memory serves as an encoding and retrieval processor. Information in the form of stimuli is encoded in accordance with explicit or implicit functions by the working memory processor. The working memory also retrieves information from previously stored material. Finally, the function of long-term memory is to store data through various categorical models or systems.

Long-term potentiation (LTP) is a persistent strengthening of synapses based on recent patterns of activity. These are patterns of synaptic activity that produce a long-lasting increase in signal transmission between two neurons. It is one of several phenomena underlying synaptic plasticity, the ability of chemical synapses to change their strength. As memories are thought to be encoded by modification of synaptic strength, LTP is widely considered one of the major cellular mechanisms that underlies learning and memory.

Cognitive disorders are a category of mental health disorders that primarily affect learning, memory, perception, and problem solving, and include amnesia, dementia, and delirium.

Delirium is a disorder that makes situational awareness and processing new information very difficult for those diagnosed. It can be accompanied by a shift in attention, mood swings, violent or unordinary behaviors, and hallucinations. It can be caused by the worsening of previous medical conditions, abuse of medications or drugs, alcohol or drug withdrawals, mental illness, severe pain, immobilization, sleep deprivation and hypnosis.

Dementia is known as a genetic or trauma induced disorder that erases part or all of the patient's memory. Dementia can have numerous causes such as genetics, brain trauma, stroke, and heart issues. Diseases that cause dementia include Alzheimer disease, Parkinson's disease, and Huntington disease.

Amnesia patients have trouble retaining long term memories. Anterograde amnesia refers to impairment of the ability to create new memories while retrograde amnesia refers to a phenomenon in which memories that were encoded or in the process of being encoded in long term memory are erased. Amnesia can be caused by concussions, traumatic brain injuries, post-traumatic stress, and alcoholism, which may cause damage to major memory encoding parts of the brain such as the hippocampus.

Cognitive disorders can also include cognitive symptoms that are frequently associated with anxiety disorders, mood disorders, and psychotic disorders having an effect on cognitive and memory functions, although these conditions may sometimes not be considered cognitive disorders per se, because loss of cognitive function is not the primary, causal symptom.

Memory disorders are disorders characterized by the hindrance to the storage, retention and recollection of memories, frequently as a result of damage to neuroanatomical structures. Memory disorders can be progressive, including Alzheimer's disease, or they can be immediate including disorders resulting from head injury.

Although some treatments are available that can improve cognition or memory, particularly in the case of particular conditions or disorders, the available treatments have limited efficacy and/or limited applicability and are characterized by side-effects. Consequently there is a need for new treatments that improve cognition or memory, or to treat cognitive disorders, memory disorders, or cognitive symptoms of disorders such as anxiety disorders, mood disorders, or psychotic disorders that have an effect on cognitive and memory functions.

SUMMARY

This disclosure relates to the treatment to improve memory or cognition, or to treat a memory or cognitive disorder, or to treat cognitive symptoms of a disease or condition by administering a T-type calcium channel antagonist. The method includes administering to a subject in need of such treatment a therapeutically effective amount of a T-type calcium channel antagonist. Also provided is the use of a T-type calcium channel antagonist for treatment to improve cognition and/or memory. The disclosure also provides the use of T-type calcium channel antagonist in the manufacture of a medicament for treatment to improve memory.

In some embodiments, the treatment improves cognition in the subject.

In some embodiments, the treatment improves memory in the subject.

In some embodiments, the treatment is for a cognitive disorder.

In some embodiments, the treatment is for a memory disorder.

In some embodiments, the treatment is for a condition selected from the group consisting of age-related cognitive impairment, agnosia, amnesia, amnestic disorder, amyotrophic lateral sclerosis, Angelman Syndrome, Asperger's syndrome, attention-deficit disorders, attention-deficit/hyperactivity disorders (ADHD), autism, cerebral amyloid angiopathy, cognitive dysfunction, cognitive impairment due to alcohol or drugs, delirium, dementia, AIDS-related dementia, alcoholic dementia, Alzheimer's disease, dementia associated with cerebral trauma, Creutzfeldt-Jakob disease and other prion-induced dementia, degenerative dementia, Huntington's disease, dementia associated with intracranial tumors, Lewy body disease, multi-infarct dementia, Parkinson's disease; Parkinsonian-ALS demential complex, Pick's disease, substance-induced persisting dementia, vascular dementia, Dravet Syndrome, head trauma, ischemia, learning disorders, learning impairment, memory impairment, memory loss, mental retardation, mild cognitive impairment, post-traumatic stress disorder, Prader-Willi Syndrome, progressive supranuclear palsy, stroke, traumatic brain injury, trisomy (including Trisomy 21 (Down Syndrome)), and Wernicke-Korsakoff's Syndrome.

In some embodiments, the treatment is for disorder that has an effect on cognitive and/or memory functions. In some embodiments, the disorder that has an effect on cognitive and/or memory functions is selected from anxiety disorders, mood disorders and psychotic disorders.

In some embodiments, the T-type calcium channel antagonist is a calcium channel antagonist that selectively targets T-type calcium channels.

In some embodiments, the T-type calcium channel antagonist is a calcium channel antagonist that selectively targets T-type calcium channels over L-type calcium channels.

In some embodiments, the T-type calcium channel antagonist is a small molecule.

In some embodiments, the T-type calcium channel antagonist is an antibody.

In some embodiments, the T-type calcium channel antagonist is a siRNA.

In some embodiments, the T-type calcium channel antagonist selectively targets Cav3.1.

In some embodiments, the T-type calcium channel antagonist selectively targets Cav3.2.

In some embodiments, the T-type calcium channel antagonist selectively targets Cav3.3.

In some embodiments, the T-type calcium channel antagonists antagonize a T-type calcium channel in a cell when the membrane potential of the cell is in the range from about −60 mV to about −30 mV, e.g., about −40 mV.

In some embodiments, the T-type calcium channel antagonist is selected from the group consisting of mibefradil, MK-8998, diltiazem, nifedipine, nitrendipine, nimodipine, niludipine, niguldipine, nicardipine, nisoldipine, amlodipine, felodipine, isradipine, ryosidine, gallopamil, verapamil, tiapamil, pimozide, thioridazine, NNC 55-0396, TTL-1177, anandamide, pimozide, penfluridol, clopimozide, fluspirilene, haloperidol, droperidol, benperidol, triperidol, melperone, lenperone, azaperone, domperidone, antrafenine, aripiprazole, ciprofloxacin, dapiprazole, dropropizine, etoperidone, itraconazole, ketoconazole, levodropropizine, mepiprazole, naftopidil, nefazodone, niaprazine, oxypertine, posaconazole, trazodone, urpidil, vesnarinone, manidipine, nilvadipine, benidipine, efonidipine, flunarizine, anandamide, lomerizine, zonisamide, U-92032, tetralol, mibefradil, NNC 55-0396, TTA-A2, TTA-A8, TTA-P1, 4-aminomethyl-4-fluoropiperidine (TTA-P2), TTA-Q3, TTA-Q6, MK-5395, MK-6526, MK-8998, Z941, Z944, phensuximide, mesuximide, desmethylmethsuximide, efonidipine, trimethadione, dimethadione, ABT-639, TTL-1177, KYSO5044, nickel, and kurtoxin, and combinations thereof.

In some embodiments, the T-type calcium channel antagonist is TTA-A2.

In some embodiments, the T-type calcium channel antagonist substantially crosses the blood brain barrier.

In some embodiments, the treatment further comprises administering to the subject an additional therapeutic agent.

In some embodiments, the additional therapeutic agent is an additional T-type calcium channel inhibitor.

Although methods and materials similar or equivalent to those described herein can be used in the practice or testing of the present invention, suitable methods and materials are described below. All publications, patent applications, patents, and other references mentioned herein are incorporated by reference in their entirety. Where the first page number of a reference is given in a citation, it is to be understood that reference is being made to the entire article cited. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF THE DRAWINGS

The drawing illustrates that cognitively deficient mice (AS) treated with vehicle alone had an LTP deficit compared to control mice, but administration of MK-8998 ("CX") at 30 mg/kg or at 60 mg/kg fully rescued the LTP deficit of the AS mice to levels similar to those observed with control (wt) mice treated with vehicle.

DETAILED DESCRIPTION

The present disclosure describes that T-type voltage-gated calcium channels are involved in Dravet syndrome (i.e., severe monoclinic epilepsy in infants; SMEI). The present disclosure further describes that modulation of such T-type voltage-gated calcium channels can be effective for the treatment of Dravet syndrome.

I. Definitions

Unless defined otherwise, all technical and scientific terms used herein have the same meaning as is commonly understood by one of ordinary skill in the art to which this disclosure belongs.

For the terms "e.g." and "such as," and grammatical equivalents thereof, the phrase "and without limitation" is understood to follow unless explicitly stated otherwise.

The singular forms "a," "an," and "the" include plural referents unless the context clearly dictates otherwise.

The term "about" means "approximately" (e.g., plus or minus approximately 10% of the indicated value).

The term "small molecule" means an organic compound with a molecular weight of about 1000 or less.

The term "subject," referring to the subject of treatment, means any animal, including mammals, e.g., human.

The phrase "therapeutically effective amount" refers to the amount of active compound or pharmaceutical agent that elicits the biological or medicinal response that is being sought in a tissue, system, animal, individual or human by a researcher, veterinarian, medical doctor or other clinician.

The term "treating" or "treatment" refers to one or more of (1) preventing a disease; e.g., preventing a disease, condition or disorder in an individual who may be predisposed to the disease, condition or disorder but does not yet experience or display the pathology or symptomatology of the disease; (2) inhibiting a disease; e.g., inhibiting a disease, condition or disorder in an individual who is experiencing or displaying the pathology or symptomatology of the disease, condition or disorder (i.e., arresting further development of the pathology and/or symptomatology); and (3) ameliorating a disease; for example, ameliorating a disease, condition or disorder in an individual who is experiencing or displaying the pathology or symptomatology of the disease, condition or disorder (i.e., reversing the pathology and/or symptomatology) such as decreasing the severity of disease or reducing or alleviating one or more symptoms of the disease.

The term "T-type calcium channel antagonists" refers to a substance that reduces the activity of T-type calcium channels, e.g., through binding to, or otherwise inhibiting or blocking activity of the channel, or through reducing the expression of T-type calcium channels.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

It is appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

The following abbreviations and symbols may be used in the present disclosure: DNA (deoxyribonucleic acid); dsRNA (double stranded RNA); g (gram); $IC_{50}$ (half maximal inhibitory concentration); kg (kilogram); mg (milligram); mRNA (messenger RNA); RNA (ribonucleic acid); RNAi (RNA interference); siRNA (small interfering RNA), wt (weight).

II. Methods of Treatment

The present disclosure provides methods for improving cognition, improving memory, treating cognitive disorders, treating memory disorders, treating cognitive symptoms of disorders that have an effect on cognitive and/or memory functions. In some embodiments, the method comprises administering a therapeutically effective amount of a T-type calcium channel antagonist as described herein, to the subject in need of the treatment. The subject of treatment can include mice, rats, other rodents, rabbits, dogs, cats, swine, cattle, sheep, horses, primates, and humans. In some embodiments, the subject is a human.

The present disclosure provides methods for improving cognition. In some embodiments, the method comprises administering a therapeutically effective amount of a T-type calcium channel antagonist as described herein, to the subject in need of the treatment.

The present disclosure provides methods for improving memory. In some embodiments, the method comprises administering a therapeutically effective amount of a T-type calcium channel antagonist as described herein, to the subject in need of the treatment.

The present disclosure provides methods of treating cognitive disorders. In some embodiments, the method comprises administering a therapeutically effective amount of a T-type calcium channel antagonist as described herein, to the subject in need of the treatment. In some embodiments, the cognitive disorders may be developmental cognitive disorders or neurocognitive disorders.

The present disclosure provides methods of treating memory disorders. In some embodiments, the method comprises administering a therapeutically effective amount of a T-type calcium channel antagonist as described herein, to the subject in need of the treatment.

The present disclosure provides methods of treating cognitive symptoms of disorders that have an effect on cognitive and/or memory functions. The disorders that have an effect on cognitive and/or memory functions include anxiety disorders, mood disorders, and psychotic disorders. In some embodiments, the method comprises administering a therapeutically effective amount of a T-type calcium channel antagonist as described herein, to the subject in need of the treatment.

In some embodiments, the treatment improves cognition in the subject.

In some embodiments, the treatment improves memory in the subject. In some embodiments, the treatment improves short term memory in the subject. In some embodiments, the treatment improves working memory in the subject. In some embodiments, the treatment improves long term memory in the subject. In some embodiments, the treatment increases long term potentiation in the subject.

In some embodiments, the cognitive disorders, memory disorders, developmental cognitive disorders, neurocognitive disorders, or disorders that have an effect on cognitive and/or memory functions (including anxiety disorders, mood disorders, and psychotic disorders) may be those as defined by the criteria set forth in the Diagnostic and Statistical Manual of Mental Disorders, Fifth Edition ("DSM 5"). Edited by American Psychiatric Association (2013).

In some embodiments, the cognitive disorders and memory disorders can include: age-related cognitive impairment, agnosia, amnesia, amnestic disorder, amyotrophic lateral sclerosis, Angelman Syndrome, Asperger's syndrome, attention-deficit disorders, attention-deficit/hyperactivity disorders (ADHD), autism, cerebral amyloid angiopathy, cognitive dysfunction, cognitive impairment due to alcohol or drugs, delirium, dementia (including AIDS-related dementia, alcoholic dementia, Alzheimer's disease (including early stage, intermediate stage or late stage Alzheimer's disease), dementia associated with cerebral trauma, Creutzfeldt-Jakob disease and other prion-induced dementia, degenerative dementia, Huntington's disease, dementia associated with intracranial tumors, Lewy body disease, multi-infarct dementia, Parkinson's disease; Parkinsonian-ALS demential complex, Pick's disease, substance-induced persisting dementia, vascular dementia), Dravet Syndrome, head trauma, ischemia, learning disorders, learning impairment, memory impairment, memory loss, mental retardation, mild cognitive impairment, post-traumatic stress disorder, Prader-Willi Syndrome, progressive supranuclear palsy, stroke, traumatic brain injury, trisomy (including Trisomy 21 (Down Syndrome)), and Wernicke-Korsakoff's Syndrome.

In some embodiments, disorders that have an effect on cognitive and/or memory functions may include anxiety disorders, mood disorders, and psychotic disorders. Anxiety disorders include generalized anxiety disorder, phobias, panic disorder, agoraphobia, social anxiety disorder, post-traumatic stress disorder, separation anxiety disorder, situational anxiety, obsessive compulsive disorder and selective mutism. Mood disorders include depressive disorders (e.g., major depressive disorder, depressive disorder, atypical depression, melancholic depression, psychotic major depression, catatonic depression, postpartum depression, seasonal affective disorder, dysthymia, double depression, depressive disorder not otherwise specified, depressive personality disorder, recurrent brief depression and minor depressive disorder), bipolar disorders (e.g., bipolar disorder, bipolar I, bipolar II, cyclothymia, bipolar disorder not otherwise specified), and substance-induced mood disorders (e.g., alcohol-induced or benzodiazepine-induced). Psychotic disorders include schizophrenia, schizophreniform disorder, schizoaffective disorder, brief psychotic disorder, delusional disorder, or chronic hallucinatory psychosis.

The disorders that may have an effect on cognitive and/or memory functions may include schizophrenia. Deficits in cognitive abilities are widely recognized as a core feature of schizophrenia. The deficits impacting the cognitive function may include deficits in working memory, long-term memory, verbal declarative memory, semantic processing, episodic memory, attention, and learning (particularly verbal learning).

The treatment can be administered at an effective dose for the particular compound. Examples of suitable doses include, in humans, include dosages in the range from about 1 mg to about 2000 mg, e.g., about 1 mg to about 2000 mg, about 2 mg to about 2000 mg, about 5 mg to about 2000 mg, about 10 mg to about 2000 mg, about 20 mg to about 2000 mg, about 50 mg to about 2000 mg, about 100 mg to about 2000 mg, about 150 mg to about 2000 mg, about 200 mg to about 2000 mg, about 250 mg to about 2000 mg, about 300 mg to about 2000 mg, about 400 mg to about 2000 mg, about 500 mg to about 2000 mg, about 1000 mg to about 2000 mg, about 1 mg to about 1000 mg, about 2 mg to about 1000 mg, about 5 mg to about 1000 mg, about 10 mg to about 1000 mg, about 20 mg to about 1000 mg, about 50 mg to about 1000 mg, about 100 mg to about 1000 mg, about 150 mg to about 1000 mg, about 200 mg to about 1000 mg, about 250 mg to about 1000 mg, about 300 mg to about 1000 mg, about 400 mg to about 1000 mg, about 500 mg to about 1000 mg, about 1 mg to about 500 mg, about 2 mg to about 500 mg, about 5 mg to about 500 mg, about 10 mg to about 500 mg, about 20 mg to about 500 mg, about 50 mg to about 500 mg, about 100 mg to about 500 mg, about 150 mg to about 500 mg, about 200 mg to about 500 mg, about 1 mg to about 250 mg, about 2 mg to about 250 mg, about 5 mg to about 250 mg, about 10 mg to about 250 mg, about 20 mg to about 250 mg, about 50 mg to about 250 mg, about 100 mg to about 250 mg, about 1 mg to about 100 mg, about 2 mg to about 100 mg, about 5 mg to about 100 mg, about 10 mg to about 100 mg, about 20 mg to about 100 mg, about 50 mg to about 100 mg. Doses can be, e.g., about 1 mg, about 2 mg, about 5 mg, about 10 mg, about 20 mg, about 50 mg, about 100 mg, about 150 mg, about 200 mg, about 250 mg, about 300 mg, about 400 mg, about 500 mg, about 1000 mg, about 1500 mg, or about 2000 mg. Doses can be less than about 2000 mg, less than about 1500 mg, less than about 1000 mg, less than about 5000 mg, less than about 400 mg, less than about 250 mg, less than about 200 mg, less than about 150 mg, less than about 100 mg, less than about 50 mg, less than about 20 mg or less than about 10 mg. Each of the doses can be doses that are administered at a frequency of once daily, twice daily, three times daily or four times daily, or less than once daily. Each of the doses can also be the dose that is administered to an adult with equivalent (scaled) dose being administered for pediatric patients.

The dose can be a dose that provides a plasma level (e.g., a steady state or a maximum level) of about 100 ng/mL, about 200 ng/mL, 500 ng/mL, about 1 µg/mL, about 2 µg/mL, about 5 µg/mL, about 10 µg/mL, about 20 µg/mL, about 50 µg/mL, about 100 µg/mL, about 200 µg/mL, about 250 µg/mL, or about 500 µg/mL, about 1000 µg/mL, or in a range between these values, or a concentration that is less than these values.

In some embodiments, treatment is continued for a period of about 1 week or longer. In some embodiments, treatment is continued for a period of about 2 weeks or longer. In some embodiments, treatment is continued for a period of about 3 weeks or longer. In some embodiments, treatment is continued for a period of about 4 weeks or longer. In some embodiments, treatment is continued for a period of about 8 weeks or longer. In some embodiments, treatment is continued for a period of about 12 weeks, or about 13 weeks, or longer. In some embodiments, treatment is continued for a period of about 24 weeks, or 26 weeks, or longer. In some embodiments, treatment is continued for a period of about 6 months or longer. In some embodiments, treatment is continued for a period of about 12 months or longer. In some embodiments, treatment is continued for a period of about 18 months or longer. In some embodiments, treatment is continued for a period of about 24 months or longer.

III. T-type Calcium Channel Antagonists

The T-type calcium channel antagonist used in any of the methods described herein, or any of the embodiments thereof, can be one or more of the T-type calcium channel agonists described below.

The T-type calcium channel antagonist can be an antagonist of human T-type calcium channels when the subject of treatment is a human.

The T-type calcium channel antagonist can be a small molecule. Example small molecule T-type calcium channel antagonists which may be used in the methods provided herein include, but are not limited to, mibefradil, diltiazem, nifedipine, nitrendipine, nimodipine, niludipine, niguldipine, nicardipine, nisoldipine, amlodipine, felodipine, isradipine, ryosidine, gallopamil, verapamil, tiapamil, pimozide, thioridazine, NNC 55-0396, TTL-1177, anandamide, benzazepine derivatives, diphenylbutylpiperidine derivatives (e.g., pimozide, penfluridol, clopimozide, and fluspirilene), butyrophenone derivatives (e.g., haloperidol, droperidol, benperidol, triperidol, melperone, lenperone, azaperone, and domperidone), and phenylpiperazine derivatives (e.g., antrafenine, aripiprazole, ciprofloxacin, dapiprazole, dropropizine, etoperidone, itraconazole, ketoconazole, levodropropizine, mepiprazole, naftopidil, nefazodone, niaprazine, oxypertine, posaconazole, trazodone, urpidil, and vesnarinone), dihydropyridine derivatives (e.g., manidipine, nilvadipine, benidipine, and efonidipine), flunarizine, anandamide, lomerizine, zonisamide, U-92032, tetralol, tetralol derivatives (e.g., mibefradil), mibefradil derivatives (e.g., NNC 55-0396 dihydrochloride), TTA-A2, TTA-A8, TTA-P1, 4-aminomethyl-4-fluoropiperidine (TTA-P2), TTA-Q3, TTA-Q6, MK-5395, MK-6526, MK-8998, Z941, Z944, succinimide anticonvulsant derivatives (e.g., ethosuximide, phensuximide, and mesuximide also known as methsuximide, N-desmethylmethsuximide also known as (alpha)-methyl-(alpha)-phenyl-succinimide), and efonidipine (e.g. (R)-efonidipine), trimethadione, dimethadione, ABT-639, TTL-1177, KYSO5044, kurtoxin. Any of the T-type calcium channel inhibitors can be in the form of a pharmaceutically acceptable salt. Structures of representative T-type calcium channel inhibitors are shown below.

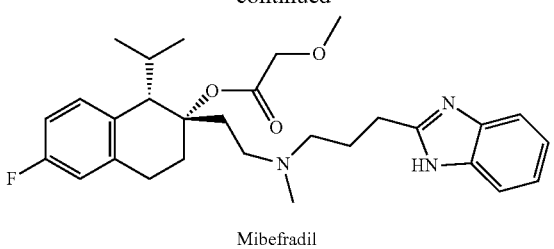

-continued

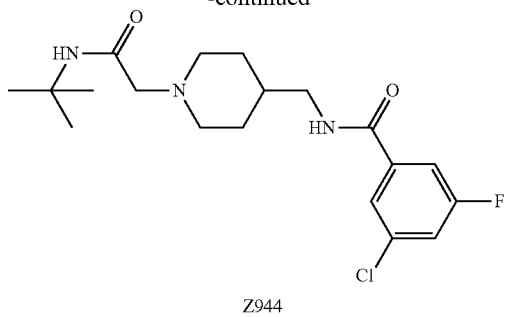

Z944

In some embodiments, T-type calcium channel small-molecule antagonist may be selected from the group consisting of those described in the patents and published patent applications listed in Giordanetto et al, "T-type calcium channels inhibitors: a patent review," *Expert Opin. Ther. Pat.,* 2011, 21, 85-101, including WO2004035000, WO9304047, WO2006098969, WO2009009015, WO2007002361, WO2007002884, WO2007120729, WO2009054982, WO2009054983, WO2009054984, US20090270413, WO2008110008, WO2009146539, WO2009146540, US8, 133,998, WO2010083264, WO2006023881, WO2006023883, WO2005007124, WO2005009392, US2005245535, WO2007073497, WO200707852, WO2008033447, WO2008033456, WO2008033460, WO2008033464, WO2008033465, WO2008050200, WO20081 17148, WO2009056934, EP1568695, WO2008007835, KR754325, U.S. Pat. No. 7,319,098, US20100004286, EP1757590, KR2009044924, US2010094006, WO2009035307, US20090325979, KR75758317, WO2008018655, US20080293786, and US20100056545, each of which is incorporated by reference in its entirety.

In some embodiments, the T-type calcium channel antagonist is a small molecule. In some embodiments, the small molecule has a molecular weight of 1000 or lower, e.g., about 900 or lower, about 800 or lower, about 700 or lower, about 600 or lower, about 500 or lower, about 400 or lower, or in the range from about 100 to about 500, about 200 to about 500, about 200 to about 400, about 300 to about 400 or about 300 to about 500.

In some embodiments, the T-type calcium channel antagonist is a selective T-type calcium channel antagonist. "Selective" in this context means that the T-type calcium channel antagonist is more potent at antagonizing T-type calcium channel calcium channels compared with other types of calcium channel, e.g., any one or more of L-type, N-type, P-type, Q-type and/or R-type calcium channels, e.g., compared with L-type calcium channels. Selectivity can be determined, e.g., by comparing the $IC_{50}$ of a compound in inhibiting T-type calcium channels with its $IC_{50}$ in inhibiting the other types of calcium channel: if the $IC_{50}$ for inhibiting T-type channels is lower than the $IC_{50}$ for inhibiting the other types of calcium channel, the compound is considered selective. An $IC_{50}$ ratio of 0.1 (or lower) denotes 10-fold (or greater) selectivity. An $IC_{50}$ ratio of 0.01 (or lower) denotes 100-fold (or greater) selectivity. An $IC_{50}$ ratio of 0.001 (or lower) denotes 1000-fold (or greater) selectivity. In some embodiments, the T-type calcium channel antagonist has selectivity for the T-type calcium channel that is 10-fold or greater, 100-fold or greater, or 1000-fold or greater compared with other types of calcium channel, e.g., any one or more of L-type, N-type, P-type, Q-type and/or R-type calcium channels, e.g., compared with L-type calcium channels.

In some embodiments, the T-type calcium channel antagonist is a selective T-type calcium channel inhibitor which is selected from the group consisting of phensuximide, methsuximide, methyl-phenyl-succinimide, R isomer of efonidipine, trimethadione, dimethadione, mibefradil, TTA-A2, TTA-A8, TTA-P1, TTA-P2, TTA-Q3, TTA-Q6, MK-5395, MK-6526, MK-8998, Z941, Z944, ABT-639, TTL-1177, KYSO5044, N C 55-0396 dihydrochloride, kurtoxin, or a derivative thereof.

In some embodiments, the T-type calcium channel antagonist is a calcium channel antagonist that selectively targets T-type calcium channels over L-type calcium channels.

In some embodiments, the T-type calcium channel antagonist is TTA-A2.

In some embodiments, the T-type calcium channel antagonist can be other than verapamil. The treatment can be carried out without administration of verapamil. In some embodiments, the T-type calcium antagonist is administered in combination with verapamil.

In some embodiments, the T-type calcium channel antagonist can be other than ethosuximide. The treatment can be carried out without administration of ethosuximide. In some embodiments, the T-type calcium antagonist is administered in combination with ethosuximide.

In some embodiments, the T-type calcium channel antagonist can be other than zonisamide. The treatment can be carried out without administration of zonisamide. In some embodiments, the T-type calcium antagonist is administered in combination with zonisamide.

In some embodiments, the T-type calcium channel antagonist can be other than dimethadione. The treatment can be carried out without administration of dimethadione. In some embodiments, the T-type calcium antagonist is administered in combination with dimethadione.

In some embodiments, the T-type calcium channel antagonist can be other than valproate. The treatment can be carried out without administration of valproate. In some embodiments, the T-type calcium antagonist is administered in combination with valproate.

In some embodiments, the T-type calcium channel antagonist can be other than topiramate. The treatment can be carried out without administration of topiramate. In some embodiments, the T-type calcium antagonist is administered in combination with topiramate.

In some embodiments, the T-type calcium channel antagonist can be other than a cannabinoid such as cannabidiol or tetrahydrocannabinol. The treatment can be carried out without administration of a cannabinoid such as cannabidiol or tetrahydrocannabinol. In some embodiments, the T-type calcium antagonist is administered in combination with a cannabinoid such as cannabidiol or tetrahydrocannabinol.

In some embodiments, the T-type calcium channel antagonist can be a molecule that does not act as a pore-blocker of the T-type calcium channel. The T-type calcium channel antagonist can be, e.g., an allosteric inhibitor of T-type calcium channels.

In some embodiments, the T-type calcium channel antagonist can be one that does not substantially affect one or more sodium channels such as sodium channels having Nav1.1, Nav1.2, Nav1.3, Nav1.4, Nav1.5, Nav1.6, Nav1.7, Nav1.8, or Nav1.9 alpha subunits, and/or Navβ1, Navβ2, Navβ3, Navβ4 subunits. The T-type calcium channel antagonist can be selective for T-type calcium channel compared to inhibition of sodium channels, e.g., having at least a 2-fold, at least a 5-fold, at least a 10-fold, at least a 20-fold, at least a 100-fold, at least a 500-fold or at least a 1000-fold selectivity (expressed, e.g., in terms of $K_i$). The T-type calcium channel inhibitor can be one that does not substantially decrease the non-inactivating sodium current in thalamocortical neurons, e.g., that decreases the inactivating sodium current by about 20% or less, about 10% or less, about 5% or less, about 2% or less, or about 1% or less.

In some embodiments, the T-type calcium channel antagonist can be one that does not substantially affect one or more potassium channels such as calcium activated potassium channels (BK channels, SK channels, IK channels), inwardly rectifying potassium channels (ROMK, GPCR regulated, ATP sensitive), tandem pore domain potassium channels (TWIK (TWIK-1, TWIK-2, KCNK7), TREK (TREK-1, TREK-2, TRAAK), TASK (TASK-1, TASK-3, TASK-5), TALK (TASK-2, TALK-1, TALK-2), THIK (THIK-1, THIK-2, TRESK), or voltage gated potassium channels (hERG, KvLQT, KvLQT2). The T-type calcium channel antagonist can be selective for T-type calcium channel compared to inhibition of potassium channels, e.g., having at least a 2-fold, at least a 5-fold, at least a 10-fold, at least a 20-fold, at least a 100-fold, at least a 500-fold or at least a 1000-fold selectivity (expressed, e.g., in terms of $K_i$).

In some embodiments, the T-type calcium channel antagonist can be one that does not substantially affect one or more GABA receptors such as $GABA_A$ receptors, $GABA_{A-\rho}$ subclass ($GABA_C$) receptors, or $GABA_B$ receptors. In some embodiments, the T-type calcium channel antagonist can be one that does not substantially affect one or more subunits of the $GABA_A$ receptors such as α-subunits (GABRA1, GABRA2, GABRA3, GABRA4, GABRA5, GABRA6), β-subunits (GABRB1, GABRB2, GABRB3), γ-subunits (GABRG1, GABRG2, GABRG3), δ-subunits (GABRD), ε-subunits (GABRE), π-subunits (GABRP), θ-subunits (GABRQ), particularly GABARA5, GABRB3 and GABRG5. The T-type calcium channel antagonist can be selective for T-type calcium channel compared to inhibition of GABA receptors, e.g., having at least a 2-fold, at least a 5-fold, at least a 10-fold, at least a 20-fold, at least a 100-fold, at least a 500-fold or at least a 1000-fold selectivity (expressed, e.g., in terms of $K_i$ or binding affinity).

In some embodiments, the T-type calcium channel antagonist can be one that does not substantially affect one or more cannabinoid receptors such as cannabinoid receptor type 1 (CB1) or cannabinoid receptor type 2 (CB2) receptors. In some embodiments, the T-type calcium channel antagonist can be one that does not substantially affect CB1 receptors. In some embodiments, the T-type calcium channel antagonist can be one that does not substantially affect CB2 receptors. The T-type calcium channel antagonist can be selective for T-type calcium channel compared to inhibition of CB1 and/or CB2 receptors, e.g., having at least a 2-fold, at least a 5-fold, at least a 10-fold, at least a 20-fold, at least a 100-fold, at least a 500-fold or at least a 1000-fold selectivity (expressed, e.g., in terms of $K_i$ or binding affinity).

In some embodiments, the T-type calcium channel antagonist can be one that does not substantially affect brain levels (e.g., CNS levels) of GABA. The T-type calcium channel antagonist can be selective for T-type calcium channel compared to increasing concentrations of GABA, e.g., having at least a 2-fold, at least a 5-fold, at least a 10-fold, at least a 20-fold, at least a 100-fold, at least a 500-fold or at least a 1000-fold selectivity (expressed, e.g., in terms of $K_i$ or binding affinity, compared with the effective dose $ED_{50}$ for increasing the concentration of GABA).

In some embodiments, the T-type calcium channel antagonist can be one that does not substantially affect one or more AMPA or kainate glutamate receptors such as AMPA receptors comprising GluR1, GluR2, GluR3 or GluR4, e.g., combining two GluR2 units with two GluR1, two GluR3 or two GluR4 units and/or kainate receptors comprising GluR5, GluR6, GluR7, KA1 and/or KA2 receptors. In some embodiments, the T-type calcium channel antagonist can be one that does not substantially affect one or more subunits of the AMPA and/or kainite receptors such as those listed above. The T-type calcium channel antagonist can be selective for T-type calcium channel compared to inhibition of AMPA or kainate receptors, e.g., having at least a 2-fold, at least a 5-fold, at least a 10-fold, at least a 20-fold, at least a 100-fold, at least a 500-fold or at least a 1000-fold selectivity (expressed, e.g., in terms of $K_i$ or binding affinity).

In some embodiments, the T-type calcium channel antagonist can be one that does not substantially inhibit histone deacetylase. The T-type calcium channel antagonist can be selective for T-type calcium channel compared to inhibition of histone deacetylase, e.g., having at least a 2-fold, at least a 5-fold, at least a 10-fold, at least a 20-fold, at least a 100-fold, at least a 500-fold or at least a 1000-fold selectivity (expressed, e.g., in terms of $K_i$ or binding affinity compared with the $IC_{50}$ for inhibition of histone deacetylase).

In some embodiments, the T-type calcium channel antagonist can be one that does not substantially inhibit GABA transaminase. The T-type calcium channel antagonist can be selective for T-type calcium channel compared to inhibition of GABA transaminase, e.g., having at least a 2-fold, at least a 5-fold, at least a 10-fold, at least a 20-fold, at least a 100-fold, at least a 500-fold or at least a 1000-fold selectivity (expressed, e.g., in terms of $K_i$ or binding affinity compared with the $IC_{50}$ for inhibition of GABA transaminase).

In some embodiments, the T-type calcium channel antagonist can be one that does not substantially inhibit succinate-semialdehyde dehydrogenase. The T-type calcium channel antagonist can be selective for T-type calcium channel compared to inhibition of succinate-semialdehyde dehydrogenase, e.g., having at least a 2-fold, at least a 5-fold, at least a 10-fold, at least a 20-fold, at least a 100-fold, at least a 500-fold or at least a 1000-fold selectivity (expressed, e.g., in terms of $K_i$ or binding affinity compared with the $IC_{50}$ for inhibition of succinate-semialdehyde dehydrogenase).

In some embodiments, the T-type calcium channel antagonist can be one that does not substantially inhibit carbonic anhydrase, or one or more isozymes thereof. The T-type calcium channel antagonist can be selective for T-type calcium channel compared to inhibition of carbonic anhydrase, e.g., having at least a 2-fold, at least a 5-fold, at least a 10-fold, at least a 20-fold, at least a 100-fold, at least a 500-fold or at least a 1000-fold selectivity (expressed, e.g., in terms of $K_i$ or binding affinity compared with the $IC_{50}$ for inhibition of carbonic anhydrase).

In some embodiments, the T-type calcium channel antagonist can be one that does not cause one or more of the following side-effects or adverse events upon administration to animals, e.g., humans: liver damage, morphological changes in the animal liver, functional changes in the animal liver, kidney damage, morphological changes in the animal kidney, functional changes in the animal kidney, systemic lupus erythematosus, suicidal thoughts, suicidal behavior, suicidal ideation, increased risk of suicide, emergence or worsening of depression, unusual changes in mood or behavior, birth defects, allergic reaction.

In some embodiments, the T-type calcium channel antagonist can be one that does not cause one or more of the following side-effects or adverse events upon administration to animals: adverse events involving the gastrointestinal system such as anorexia, vague gastric upset, nausea and vomiting, cramps, epigastric and abdominal pain, weight loss, diarrhea, gum hypertrophy and swelling of the tongue; adverse events involving the hemopoietic system such as leukopenia, agranulocytosis, pancytopenia, with or without bone marrow suppression, and eosinophilia; adverse events involving the nervous system, including neurological reactions, sensory reactions, or psychiatric or psychological aberrations such as drowsiness, headache, dizziness, euphoria, hiccups, irritability, hyperactivity, lethargy, fatigue, ataxia, confusion, disturbances of sleep, night terrors, inability to concentrate, aggressiveness, paranoid psychosis, increased libido, or increased state of depression with overt suicidal intentions; adverse events involving the integumentary system including dermatologic manifestations such as urticaria, Stevens-Johnson syndrome, systemic lupus erythematosus, pruritic erythematous rashes, and hirsutism; adverse events involving the special senses such as myopia; and adverse events involving the genitourinary system, such as vaginal bleeding or microscopic hematuria.

In some embodiments, the T-type calcium channel antagonist is an antibody. Various methods for the preparation of antibodies are known in the art. See, Antibodies: A Laboratory Manual, CSH Press, Eds., Harlow, and Lane (1988); Harlow, Antibodies, Cold Spring Harbor Press, N.Y. (1989). For example, antibodies can be prepared by immunizing a suitable mammalian host with a sample of whole cells isolated from a patient. Antibodies can be produced by cell culture techniques, including the generation of monoclonal antibodies as described herein, or via transfection of antibody genes into suitable bacterial or mammalian cell hosts, in order to allow for the production of recombinant antibodies.

In some embodiments, the antibody is a monoclonal antibody. A "monoclonal antibody" is an antibody obtained from a population of substantially homogeneous antibodies, i.e., the antibodies comprising the population are identical except for possible naturally occurring mutations that are present in minor amounts.

In some embodiments, an antibody provided herein can be produced by recombinant means. In some embodiments, the antibody is a "humanized" or human antibody. "Humanized" or human antibodies can also be produced, and are preferred for use in therapeutic contexts. Methods for humanizing murine and other non-human antibodies, by substituting one or more of the non-human antibody sequences for corresponding human antibody sequences, are well known. See, e.g., Jones et al., Nature, 1986, 321, 522-25; Riechmann et al., Nature, 1988, 332, 323-27; Verhoeyen et al., Science, 1988, 239, 1534-36, Carter et al., Proc. Natl. Acad. Sci. USA, 1993, 89, 4285; and Sims et al., J. Immunol., 1993, 151, 2296. These humanized antibodies are designed to minimize unwanted immunological response toward rodent antihuman antibody molecules which limits the duration and effectiveness of therapeutic applications of those moieties in human recipients. Accordingly, preferred antibodies used in the therapeutic methods described herein are those that are either fully human or humanized with high affinity but exhibit low or no antigenicity in the subject.

In some embodiments, the T-type calcium channel antagonist is an oligonucleotide inhibitor. Example oligonucleotide inhibitors include, but are not limited to, anti-sense oligonucleotides, RNAi, dsRNA, siRNA and ribozymes. In some embodiments, the T-type calcium channel antagonist is a siRNA. As used in the specification, "antisense oligonucleotide" refers to a stretch of single-stranded DNA or RNA, usually chemically modified, whose sequence (3'-5') is complementary to the sense sequence of a molecule of mRNA. Antisense molecules effectively inhibit gene expression by forming RNA/DNA duplexes. Antisense is understood to work by a variety of mechanisms, including physically blocking the ability of ribosomes to move along the messenger RNA, and hastening the rate at which the mRNA is degraded within the cytosol.

In order to avoid digestion by DNAse, antisense oligonucleotides can be chemically modified. For example, phosphorothioate oligodeoxynucleotides are stabilized to resist nuclease digestion by substituting one of the non-bridging phosphoryl oxygen of DNA with a sulfur moiety. Increased antisense oligonucleotide stability can also be achieved using molecules with 2-methoxyethyl (MOE) substituted backbones as described generally in U.S. Pat. No. 6,451,991, incorporated by reference, and U.S. Pat. Appl. Publ. No. 2003/0158143-A1. Thus, the antisense oligonucleotide can be modified to enhance in vivo stability relative to an unmodified oligonucleotide of the same sequence. The modification may be, e.g., a (2'-O-2-methoxyethyl) modification. The oligonucleotide may have a phosphorothioate backbone throughout, the sugar moieties of nucleotides 1-4 and 18-21 may bear 2'-O-methoxyethyl modifications and the remaining nucleotides may be 2'-deoxynucleotides.

It is understood in the art that an antisense oligonucleotide need not have 100% identity with the complement of its target sequence in order to be effective. The antisense oligonucleotides, therefore, can have a sequence that is at least about 70% identical to the complement of the target sequence. In one embodiment, the antisense oligonucleotides have can a sequence that is at least about 80% identical to the complement of the target sequence. In other embodiments, they have a sequence that is at least about 90% identical or at least about 95% identical to the complement of the target sequence, allowing for gaps or mismatches of several bases. Identity can be determined, for example, by using the BLASTN program of the University of Wisconsin Computer Group (GCG) software.

The antisense oligonucleotides according to the present invention are typically between 7 and 100 nucleotides in length. In one embodiment, the antisense oligonucleotides comprise from about 7 to about 50 nucleotides, or nucleotide analogues. In another embodiment, the antisense oligonucleotides comprise from about 7 to about 35 nucleotides, or nucleotide analogues. In other embodiments, the antisense oligonucleotides comprise from about 12 to about 35 nucleotides, or nucleotide analogues, and from about 15 to about 25 nucleotides, or nucleotide analogues.

The oligonucleotide inhibitors according to the present invention can be siRNA molecules that are targeted to a gene of interest such that the sequence of the siRNA corresponds to a portion of said gene. RNA molecules used in the present invention generally comprise an RNA portion and some additional portion, for example a deoxyribonucleotide portion.

The present disclosure further contemplates ribozyme oligonucleotide modulators that specifically target mRNA encoding a protein of interest, such as the proteins comprising the T-type calcium channel. Ribozymes are RNA molecules having an enzymatic activity that enables the ribozyme to repeatedly cleave other separate RNA molecules in a nucleotide-sequence specific manner. Such enzymatic RNA molecules can be targeted to virtually any mRNA transcript, and efficient cleavage can be achieved in vitro. Kim et al., *Proc. Natl. Acad. Sci. USA,* 1987, 84, 8788; Haseloff et al., *Nature,* 1988, 334, 585; Cech, *JAMA,* 1988, 260, 3030; and Jefferies et al., *Nucleic Acids Res.,* 1989, 17, 1371.

Typically, a ribozyme comprises two portions held in close proximity: an mRNA binding portion having a sequence complementary to the target mRNA sequence and a catalytic portion which acts to cleave the target mRNA. A ribozyme acts by first recognizing and binding a target mRNA by complementary base-pairing through the target mRNA binding portion of the ribozyme. Once it is specifically bound to its target, the ribozyme catalyzes cleavage of the target mRNA. Such strategic cleavage destroys the ability of a target mRNA to direct synthesis of an encoded protein. Having bound and cleaved its mRNA target, the ribozyme is released and can repeatedly bind and cleave new target mRNA molecules.

In some embodiments, the selective T-type calcium channel antagonist substantially crosses the blood brain barrier.

In some embodiments, the selective T-type calcium channel antagonist does not substantially cross the blood brain barrier.

In some embodiments, the T-type calcium channel antagonist is a calcium channel antagonist that selectively targets T-type calcium channels. In some embodiments, the T-type calcium channel antagonist is a small molecule as described herein.

In some embodiments, the T-type calcium channel antagonist selectively targets Cav3.1. In some embodiments, the T-type calcium channel antagonist selectively targets Cav3.2. In some embodiments, the T-type calcium channel antagonist selectively targets Cav3.3. "Selective" in this context means that the T-type calcium channel antagonist is more potent at antagonizing one type of T-type calcium channel over another type of calcium channel, e.g., more potent at antagonizing Cav3.1 than Cav3.2 or Cav3.3 or both; more potent at antagonizing Cav3.2 than Cav3.1 or Cav3.3 or both; more potent at antagonizing Cav3.3 than Cav3.1 or Cav3.2 or both. Selectivity can be determined, e.g., by comparing the $IC_{50}$ of a compound in inhibiting one type of T-type calcium channel with its $IC_{50}$ in inhibiting the other types of T-type calcium channel: if the $IC_{50}$ for inhibiting one type of T-type channels is lower than the $IC_{50}$ for inhibiting the other type of T-type calcium channel, the compound is considered selective. An $IC_{50}$ ratio of 0.1 (or lower) denotes 10-fold (or greater) selectivity. An $IC_{50}$ ratio of 0.01 (or lower) denotes 100-fold (or greater) selectivity. An $IC_{50}$ ratio of 0.001 (or lower) denotes 1000-fold (or greater) selectivity. In some embodiments, the selectivity for Cav3.1, Cav3.2 or Cav3.3 is 10-fold or greater, 100-fold or greater, or 1000-fold or greater.

In some embodiments, the T-type calcium channel antagonist selectively targets T-type calcium channels (e.g., Cav3.1, Cav3.2, and/or Cav3.3) over sodium channels such as sodium channels having Nav 1.1, Nav 1.2, Nav 1.3, Nav 1.4, Nav 1.5, Nav 1.6, Nav 1.7, Nav 1.8, or Nav 1.9 alpha subunits, and/or Nav β1, Nav β2, Nav β3, Nav β4 subunits. The T-type calcium channel antagonist can be selective for T-type calcium channel compared to inhibition of sodium channels. Selectivity can be determined, e.g., by comparing the $IC_{50}$ of a compound in inhibiting one or more of the types of T-type calcium channel with its $IC_{50}$ in inhibiting the one or more types of sodium channel: if the $IC_{50}$ for inhibiting the T-type calcium channels is lower than the $IC_{50}$ for inhibiting the sodium channel, the compound is considered selective. An $IC_{50}$ ratio of 0.1 (or lower) denotes 10-fold (or greater) selectivity. An $IC_{50}$ ratio of 0.01 (or lower) denotes 100-fold (or greater) selectivity. An $IC_{50}$ ratio of 0.001 (or lower) denotes 1000-fold (or greater) selectivity. In some embodiments, the selectivity for T-type calcium channels is 10-fold or greater, 100-fold or greater, or 1000-fold or greater.

The effectiveness of a compound in inhibiting T-type calcium channels may vary depending on the state of the T-type calcium channel that the T-type calcium channel antagonist inhibits. T-type calcium channels can occur in different states depending on the cell membrane potential. T-type calcium channel antagonists that are effective in the methods described herein may include T-type calcium channel antagonists that block T-type calcium channels when the membrane potential is in the range from about −60 mV to about −30 mV, e.g., preferably about −40 mV. A membrane potential "in the range from about −60 to about −30 mV" can include membrane potentials within a range of −70 mV to −20 mV, or within a range of −65 mV to −25 mV, and can also encompass membrane potential ranges such as about −40 mV to about −30 mV, about −50 mV to about −30 mV, about −70 mV to about −30 mV, about −50 mV to about −40 mV, about −60 mV to about −40 mV, about −70 mV to about −40 mV, about −60 mV to about −50 mV, and about −70 to about −50 mV, as well as about −30 mV, about −40 mV, about −50 mV, and about −60 mV. In some embodiments, the T-type calcium channel antagonists that are effective in the methods described herein may include T-type calcium channel antagonists that block T-type calcium channels when the membrane potential is in the range from about −100 mV to about −80 mV, e.g., preferably about −90 mV. A membrane potential "in the range from about −100 to about −80 mV" can include membrane potentials within a range of −110 mV to −70 mV, or within a range of −105 mV to −75 mV, and can also encompass membrane potential ranges such as about −100 mV to about −80 mV, about −90 mV to about −80 mV, and about −100 mV to about −90 mV, as well as about −100 mV, about −90 mV, and about −80 mV.

While not being limited by any theory, it is believed that T-type calcium channel antagonists that are effective in the methods described herein may include T-type calcium channel antagonists that block T-type calcium channels when the membrane potential is in the range from about −60 mV to about −30 mV, e.g., about −40 mV selectively when compared to blockade of the T-type calcium channels when the membrane potential is in the range from about −100 mV to about −80 mV, e.g., about −90 mV.

A T-type channel inhibitor that is effective may inhibit T-type calcium channels with an $IC_{50}$ for inhibiting T-type calcium channels when the membrane potential is about −40 mV that is about 10 μM or lower, e.g., about 1 μM or lower, about 500 nM or lower, about 100 nM or lower, about 50 nM or lower, about 10 nM or lower, about 5 nM or lower, or about 1 nM or lower. A T-type calcium channel antagonist that is effective may inhibit T-type calcium channels at a membrane potential of about −40 mV selectively compared to inhibition of T-type calcium channels at a membrane potential of about −90 mV. For example, the ratio of the $IC_{50}$ of the T-type calcium channel antagonist in inhibiting T-type calcium channels at a membrane potential of about −40 mV selectively compared to inhibition of T-type calcium channels at a membrane potential of about −90 mV may be about 1:2 or lower, e.g., about 1:5 or lower, about 1:10 or lower, about 1:20 or lower, about 1:50 or lower, about 1:100 or lower, about 1:500 or lower, about 1:1000 or lower. In some embodiments, the selectivity for inhibiting T-type calcium channels at about −40 mV compared to inhibiting T-type calcium channels at about −90 mV is 2-fold or greater, 5-fold or greater, 10-fold or greater, 100-fold or greater, or 1000-fold or greater.

A T-type channel inhibitor that is effective may inhibit T-type calcium channels with an $IC_{50}$ for inhibiting T-type calcium channels when the membrane potential is about −90 mV that is about 10 μM or lower, e.g., about 1 μM or lower, about 500 nM or lower, about 100 nM or lower, about 50 nM or lower, about 10 nM or lower, about 5 nM or lower, or about 1 nM or lower. A T-type calcium channel antagonist that is effective may inhibit T-type calcium channels at a membrane potential of about −90 mV selectively compared to inhibition of T-type calcium channels at a membrane potential of about −40 mV. For example, the ratio of the $IC_{50}$ of the T-type calcium channel antagonist in inhibiting T-type calcium channels at a membrane potential of about −90 mV selectively compared to inhibition of T-type calcium channels at a membrane potential of about −40 mV may be about 1:2 or lower, e.g., about 1:5 or lower, about 1:10 or lower, about 1:20 or lower, about 1:50 or lower, about 1:100 or lower, about 1:500 or lower, about 1:1000 or lower. In some embodiments, the selectivity for inhibiting T-type calcium channels at about −90 mV compared to inhibiting T-type calcium channels at about −40 mV is 2-fold or greater, 5-fold or greater, 10-fold or greater, 100-fold or greater, or 1000-fold or greater.

All compounds, and pharmaceutically acceptable salts thereof, can be found together with other substances such as water and solvents (e.g. hydrates and solvates) or can be isolated. In some embodiments, the compounds provided herein, or pharmaceutically acceptable salts thereof, are substantially isolated. By "substantially isolated" is meant that the compound is at least partially or substantially separated from the environment in which it was formed or detected. Partial separation can include, for example, a composition enriched in the compounds provided herein. Substantial separation can include compositions containing at least about 50%, at least about 60%, at least about 70%, at least about 80%, at least about 90%, at least about 95%, at least about 97%, or at least about 99% by weight of the compounds provided herein, or salt thereof. Methods for isolating compounds and their salts are routine in the art.

As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present application include the conventional non-toxic salts of the parent compound formed, for example, from non-toxic inorganic or organic acids. The pharmaceutically acceptable salts of the present application can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso- propanol, or butanol) or acetonitrile are preferred. Lists of suitable salts are found in *Remington's Pharmaceutical Sciences*, 17th ed., Mack Publishing Company, Easton, Pa., 1985, p. 1418 and *Journal of Pharmaceutical Science*, 66, 2 (1977). Methods for preparing salt forms are described, for example, in *Handbook of Pharmaceutical Salts: Properties, Selection, and Use*, Wiley-VCH, 2002.

IV. Combination Therapies

One or more additional therapeutic agents can be used in combination with the compounds provided herein for treatment to improve memory and/or cognition. Example additional therapeutic agents include, but are not limited to calcium channel antagonists (including L-type and T-type calcium channel antagonists), The combination of the drugs is may safer or more effective than either drug alone. Additionally, the compounds of the invention may be used in combination with one or more other drugs that treat, prevent, control, ameliorate, or reduce the risk of side effects or toxicity of the compounds of the invention. Such other drugs may be administered, by a route and in an amount commonly used therefor, contemporaneously or sequentially with the compounds of the present invention. Accordingly, the pharmaceutical compositions of the present invention include those that contain one or more other active ingredients, in addition to a T-type calcium channel inhibitor. The combinations may be administered as part of a unit dosage form combination product, or as a kit or treatment protocol wherein one or more additional drugs are administered in separate dosage forms as part of a treatment regimen.

In some embodiments, the treatment with the T-type calcium channel antagonist can be provided in the absence of additional therapeutic agents useful for improving cognition and/or memory. In some embodiments, the treatment can be performed with a single T-type calcium channel antagonist. In some embodiments, the treatment with the T-type calcium channel antagonist can be provided in the absence of an additional therapeutic agent for treating the disease or condition being treated.

Example calcium channel antagonists include, but are not limited to, the T-type calcium channel antagonists described herein, and L-type calcium channel antagonists. In some embodiments, the additional calcium channel antagonist is selected from a T-type calcium channel antagonist provided herein. In some embodiments, the additional calcium channel antagonist is an L-type calcium channel antagonist. In some embodiments, the additional calcium channel antagonist is a T-type calcium channel antagonist. In some embodiments, the additional calcium channel antagonist is a T-type calcium channel antagonist selected from the group consisting of mibefradil, MK-5395, MK-6526, MK-8998, and Z944. In some embodiments, the additional calcium channel antagonist is a T-type calcium channel antagonist and an L-type calcium channel antagonist. In some embodiments, the additional calcium channel antagonist is a T-type calcium channel antagonist or an L-type calcium channel antagonist selected from the group consisting of ACT-28077, mibefradil, and TTL-1177. In some embodiments, the additional calcium channel antagonist is mibefradil.

For the treatment of Alzheimer's disease, mild cognitive impairment, or a related condition, the T-type calcium channel inhibitor may be employed in combination with an acetylcholinesterase inhibitors such as donepezil and rivastigmine, an NMDA antagonist such as memantine, a muscarinic receptor modulator, an AMPA receptor modulator, an mGluR3 receptor modulators, nicotinic alpha-7 and/or alpha4 beta 2 receptor modulator, an 5-HT6 or 5-HT4 receptor modulator, a modulator of phosphodiesterases (PDEs), an alpha 2c receptor anagonists, a histone deacetylases, or antioxidant therapies.

The T-type calcium channel inhibitor may be employed in combination with therapies that may alter or modify the course of disease progression, including beta-amyloid modulating therapies such as BACE1 inhibitors, gamma-secretase modulators, tau and/or phosphor-tau modulators, and biologic therapies which modulate plaques associated with neurological disorders including antibodies, RNAi, miRNA, and cell-therapies.

In certain embodiments (for example, for the treatment of a cognitive disorder, and/or a condition characterized by neurodegeneration, such Alzheimer's disease or Parkinson's disease) the T-type calcium channel inhibitor can be employed in combination with, e.g., donepezil, tacrine, rivastigmine, memantine (AXURA®, AKATINOL®, NAMENDA®, EBIXA®, ABIXA®), aricept, physostigmine, nicotine, arecoline, huperzine alpha, selegiline, Rilutek® (riluzole), Levodopa with carbidopa (SINEMET® or SINEMET CR®), Levodopa with benserazide (PROLOPA® or MADOPAR®), entacapone (COMTAN® or TASMAR®), dopamine agonists (such as pramiprexole (MIRAPEX®), ropinerole (REQUIP®), bromocriptine (PARLODEL®) and pergolide (PERMAX®), amantadine (SYMMETREL®), benztropine (COGENTIN®), trihexphenydil (ARTANE®), deprenyl (ELDEPRYL®), and the like.

In certain embodiments (for example, for the treatment of schizophrenia, bipolar disorder, and the like) the neuropharmaceutical may be an antipsychotic drug. Examples of antipsychotic drugs include, but are not limited to, butyrophenone (for example, Haloperidol (HALDOL®) and Droperidol (DROLEPTAN®)); phenothiazine (for example, chlorpromazine (THORAZINE®), fluphenazine (PROLIXIN®), perphenazine (TRILAFON®), prochlorperazine (COMPAZINE®), thioridazine (MELLARIL®), trifluoperazine (STELAZINE®), mesoridazine, promazine, triflupromazine (VESPRIN®), levomepromazine (NOZINAN®) and promethazine (PHENERGAN®)); thioxanthene (for example, chlorprothixene (CLOXAN®, TARACTAN®, TRUXAL®), Clopenthixol (SORDINAL®), flupenthixol (DEPIXOL®, FLUANXOL®), thiothixene (NAVANE®) and zuclopenthixol (CLOPIXOL®, ACUPHASE®)); clozapine (CLOZARIL®); olanzapine (ZYPREXA®); risperidone (RISPERDAL®, RISPERDAL CONSTA®); quetiapine (SEROQUEL®); ziprasidone (GEODON®); amisulpride (SOLIAN®); asenapine (SAPHRIS®); paliperidone (INVEGA®); Iloperidone (FANAPT®); Zotepine (NIPOLEPT®, LOSIZOPILON®, LODOPIN®, SETOUS®); Sertindole (SERDOLECT®); Aripiprazole (ABILIFY®); dopamine partial agonists (BIFEPRUNOX®, NORCLOZAPINE® (ACP-104)); lamotrigine (LAMICTAL®); memantine (AXURA®, AKATINOL®, NAMENDA®, EBIXA®, ABIXA®); tetrabenazine (NITOMAN®, XENAZINE®); cannabidiol; LY2140023, and the like.

In certain embodiments (for example, for the treatment of depression, panic disorder, social phobia, generalized anxiety disorder (GAD), and the like) the T-type calcium channel inhibitor may be employed in combination with an antidepressant and/or mood stabilizer. Examples of antidepressants include, but are not limited to, a tricyclic antidepressant (for example, IMIPRAMINE® and variants); a selective serotonin reuptake inhibitor (SSRI) (for example, fluoxetine (PROZAC®), paroxetine (PAXIL®, SEROXAT®), escitalopram (LEXAPRO®, ESIPRAM®), citalopram (CELEXA®), sertraline (ZOLOFT®) and fluvoxamine (LUVOX®)); a serotonin-norepinephrine reuptake inhibitor (SNRT) (for example, venlafaxine (EFFEXOR®)); milnacipram and duloxetine (CYMBALTA®); a noradrenergic and specific serotonergic antidepressant (NASSA) (for example, mirtazapine (AVANZA®, ZISPIN®, REMERON®) and mianserin); a norepinephrine (noradrenaline) reuptake inhibitor (NRI) (for example, reboxetine (EDRONAX®)); a norepinephrine-dopamine reuptake inhibitor (for example, bupropion (WELLBUTRIN®, ZYBAN®)); Amitriptyline; Nortriptiline; Protriptyline; Desipramine; Trimipramine; Amoxapine; Bupropion; Bupropion SR; S-Citalopram; Clomipramine; Doxepin; Isocarboxazid; Velafaxine XR; Tranylcypromine; Trazodone; Nefazodone; Phenelzine; Lamatrogine; Lithium; Topiramate; Gabapentin; Carbamazepine; Oxacarbazepine; Valporate; Maprotiline; Mirtazapine; Brofaromine; Gepirone; Moclobemide; isoniazid; iproniazid, and the like.

In certain embodiments (for example, for the treatment of ADD or ADHD), the T-type calcium channel inhibitor may be employed in combination with an ADHD medication such as a statin, amphetamine, Modafinil, Desoxyn, methamphetamine, cocaine, arecoline, Dexmethylphenidate (Focalin, Focalin XR), dextroamphetamine (Dexedrine, Dexedrine Spansules, Dextroamphetamine ER, Dextrostat), methylphenidate (Concerta, Daytrana, Metadate CD, Metadate ER, Methylin, Methylin ER, Ritalin, Ritalin-LA, Ritalin-SR), lisdexamfetamine dimesylate (Vyvanse), mixed salts amphetamine (Adderall, Adderall XR), Atomoxetine (Strattera), clonidine hydrochloride (Catapres), guanfacine hydrochloride (Tenex), arecoline, or Pemoline.

In some embodiments, the therapy can be administered as a monotherapy. In some embodiments, the therapy can be administered in the absence of additional antiepileptic therapy. The therapy can be administered in the absence of any of the additional agents described in this section. For example, the therapy can be administered in the absence of additional agents.

The one or more additional therapeutic agents can be administered to a patient simultaneously or sequentially, using the same schedule or a different schedule of administration, which will be determined by the particular combination used and the judgment of the prescribing physician.

V. Pharmaceutical Compositions

The T-type calcium channel inhibitors used in the methods described herein can be administered in the form of pharmaceutical compositions. Thus the present disclosure provides T-type calcium channel inhibitor, and at least one pharmaceutically acceptable carrier for use in the claimed methods of treatment, or the manufacture of a medicament for treating conditions as described herein. These compositions can be prepared in a manner known in the pharmaceutical art, and can be administered by a variety of routes. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, e.g., by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This application provides pharmaceutical compositions which contain, as the active ingredient, a T-type calcium channel inhibitor (which can be in the form of a pharmaceutically acceptable salt), in combination with one or more pharmaceutically acceptable carriers (excipients). In some embodiments, the composition is suitable for topical administration. In making the compositions of the invention, the active ingredient is typically mixed with an excipient, diluted by an excipient or enclosed within such a carrier in the form of, e.g., a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, e.g., up to 10% by weight of the active compound, soft and hard gelatin capsules, suppositories, sterile injectable solutions and sterile packaged powders.

In preparing a formulation, the T-type calcium channel inhibitor can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g., about 40 mesh.

The compounds of the invention may be milled using known milling procedures such as wet milling to obtain a particle size appropriate for tablet formation and for other formulation types. Finely divided (nanoparticulate) preparations of the compounds of the invention can be prepared by processes known in the art.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup and methyl cellulose. The Formulations can additionally include: lubricating agents such as talc, magnesium stearate and mineral oil; wetting agents; emulsifying and suspending agents; preserving agents such as methyl- and propylhydroxy-benzoates; sweetening agents; and flavoring agents.

In some embodiments, the pharmaceutical composition comprises silicified microcrystalline cellulose (SMCC) and at least one compound described herein, or a pharmaceutically acceptable salt thereof. In some embodiments, the silicified microcrystalline cellulose comprises about 98% microcrystalline cellulose and about 2% silicon dioxide wt/wt.

In some embodiments, a wet granulation process is used to produce the composition.

In some embodiments, a dry granulation process is used to produce the composition.

The compositions can be formulated in a unit dosage form, each dosage containing from about 5 to about 1,000 mg (1 g), more usually about 100 mg to about 500 mg, of the active ingredient. In some embodiments, each dosage contains about 10 mg of the active ingredient. In some embodiments, each dosage contains about 50 mg of the active ingredient. In some embodiments, each dosage contains about 25 mg of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The components used to formulate the pharmaceutical compositions are of high purity and are substantially free of potentially harmful contaminants (e.g., at least National Food grade, generally at least analytical grade, and more typically at least pharmaceutical grade). Particularly for human consumption, the composition is preferably manufactured or Formulated under Good Manufacturing Practice standards as defined in the applicable regulations of the U.S. Food and Drug Administration. For example, suitable Formulations may be sterile and/or substantially isotonic and/or in full compliance with all Good Manufacturing Practice regulations of the U.S. Food and Drug Administration.

The active compound may be effective over a wide dosage range and is generally administered in a therapeutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms and the like.

The therapeutic dosage of a compound of the present invention can vary according to, e.g., the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 $\mu$g/kg to about 1 g/kg of body weight per day. In some embodiments, the dose range is from about 0.01 mg/kg to about 100 mg/kg of body weight per day. The dosage is likely to depend on such variables severity of the disease, the overall health status of the particular patient, the relative biological efficacy of the compound selected, Formulation of the excipient, and its route of administration. Effective doses can be extrapolated from dose-response curves derived from in vitro or animal model test systems. Effective doses for a human can be, e.g., about 1 mg, 2 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 110 mg, 120 mg, 125 mg, 130 mg, 140 mg, 150 mg, 160 mg, 170 mg, 180 mg, 190 mg, 200 mg, 250 mg, 300 mg, 350 mg, 400 mg, 500 mg, 600 mg, 700 mg, 800 mg, 900 mg or 1000 mg. The doses can be administered, e.g., once a day, twice a day, three times a day, or four times a day.

In some embodiments, when the T-type calcium channel antagonist is mibefradil, and the mibefradil can be administered at a dose of, e.g., about 0.1 mg, 0.3 mg, 1 mg, 3 mg, 5 mg, 10 mg. 15 mg. or 30 mg. The doses can be administered, e.g., once a day, twice a day, three times a day, or four times a day.

In some embodiments, when the T-type calcium channel antagonist is MK-5395, and the MK-5395 can be administered at a dose of, e.g., about 0.3 mg/kg, 1 mg/kg, 3 mg/kg, 5 mg/kg, 10 mg/kg. 30 mg/kg, or 100 mg/kg. The doses can be administered, e.g., once a day, twice a day, three times a day, or four times a day.

In some embodiments, the T-type calcium channel antagonist is MK-6526, and the MK-6526 can be administered at a dose of, e.g., about 0.3 mg/kg, 1 mg/kg, 3 mg/kg, 5 mg/kg, 10 mg/kg. 30 mg/kg, or 100 mg/kg. The doses can be administered, e.g., once a day, twice a day, three times a day, or four times a day.

In some embodiments, the T-type calcium channel antagonist is MK-8998, and the MK-8998 can be administered at a dose of, e.g., about 0.3 mg/kg, 1 mg/kg, 3 mg/kg, 5 mg/kg, 10 mg/kg. 30 mg/kg, or 100 mg/kg. The doses can be administered, e.g., once a day, twice a day, three times a day, or four times a day.

In some embodiments, the T-type calcium channel antagonist is Z944, and the Z944 can be administered at a dose of, e.g., about 0.3 mg/kg, 1 mg/kg, 3 mg/kg, 5 mg/kg, 10 mg/kg. 30 mg/kg, or 100 mg/kg. The doses can be administered, e.g., once a day, twice a day, three times a day, or four times a day.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, e.g., about 0.1 to about 1000 mg of the active ingredient of the present invention.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face mask, tent, or intermittent positive pressure breathing machine. Solution, suspension, or powder compositions can be administered orally or nasally from devices which deliver the Formulation in an appropriate manner.

Topical formulations can contain one or more carriers. In some embodiments, ointments can contain water and one or more hydrophobic carriers selected from, e.g., liquid paraffin, polyoxyethylene alkyl ether, propylene glycol, white petroleum jelly, and the like. Carrier compositions of creams can be based on water in combination with glycerol and one or more other components, e.g., glycerinemonostearate, PEG-glycerinemonostearate and cetylstearyl alcohol. Gels can be formulated using isopropyl alcohol and water, suitably in combination with other components such as, e.g., glycerol, hydroxyethyl cellulose, and the like. In some embodiments, topical formulations contain at least about 0.1, at least about 0.25, at least about 0.5, at least about 1, at least about 2 or at least about 5 wt % of the compound of the invention.

The amount of compound or composition administered to a patient will vary depending upon what is being administered, the purpose of the administration, such as prophylaxis or therapy, the state of the patient, the manner of administration and the like. In therapeutic applications, compositions can be administered to a patient already suffering from a disease in an amount sufficient to eliminate or at least partially alleviate the symptoms of the disease and its complications. Effective doses will depend on the disease condition being treated as well as by the judgment of the attending clinician depending upon factors such as the severity of the disease, the age, weight and general condition of the patient and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers or stabilizers will result in the formation of pharmaceutical salts.

The therapeutic dosage of a T-type calcium channel antagonist used in the methods described herein can vary according to, e.g., the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the T-type calcium channel antagonists can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or in vivo model test systems.

EXAMPLES

The invention is further described in the following example, which does not limit the scope of the invention defined in the claims.

Example 1

Effect of a T-Type Calcium Channel Inhibitor (MK-8998) on LTP Deficits in Cognitively Deficient Mice For all behavioral and electrophysiology experiments female Ube3am−/p+ KO mice (i.e., AS mice) were crossed with wild-type males, to generate heterozygous AS mice and littermate controls in the F1 hybrid 129S2-057BL/6 background. The AS mice have cognitive deficits, including long term potentiation (LTP) deficits.

LTP Protocol

Control mice ("wt") were treated with vehicle while AS mice were treated with vehicle or MK-8998 ("CX") at 30 mg/kg or at 60 mg/kg dose given orally twice per day in the morning and afternoon. Dosing was carried out for one week before testing, then behavioral tests were carried out on the animals over a 5-week period.

After the behavioural tests, animals remained under treatment until the animals were sacrificed one hour after the last drug administration. After the animals had been sacrificed, sagittal slices (400 μm) were made using a vibratome and submerged in ice-cold artificial CSF (ACSF), and hippocampi were dissected out. These sagittal hippocampal slices were maintained at room temperature for at least 1.5 h to recover before experiments were initiated. Then they were placed in a submerged recording chamber and perfused continuously at a rate of 2 ml/min with ACSF at 31° C., equilibrated with 95% $O_2$ and 5% $CO_2$. ACSF contained the following (in mM): 120 NaCl, 3.5 KCl, 2.5 $CaCl_2$, 1.3 $MgSO_4$, 1.25 $NaH_2PO_4$, 26 $NaHCO_3$, and 10 D-glucose. Extracellular recording of field EPSP (fEPSPs) were made in CA1 stratum radiatum with platinum/iridium (Pt/Ir) electrodes (FHC). A bipolar Pt/Ir (FHC) was used to stimulate Schaffer-collateral/commissural afferents with a stimulus duration of 100 μs. LTP was evoked using the 10 Theta burst protocol (10 trains of 4 stimuli at 100 Hz, 200 ms apart), performed at two-third of the maximum fEPSP. fEPSP sizes were recorded once per minute. Potentiation was measured as the normalized increase of the mean fEPSP slope for the duration of the baseline. Only stable recordings were included, and this judgment was made blind to genotype. Final LTP was determined over the last 10 min of the recording.

LTP Results and Conclusion:

After the behavioural tests, animals remained on treatment until the animal was sacrificed in order to determine synaptic plasticity in hippocampal slices. The mice were divided in two groups for the LTP measurements. Electrodes were replaced between these experiments. This design reduces experimental variability, but does not allow cross-comparison between drugs.

LTP was evoked using the 10 Theta burst protocol (10 trains of 4 stimuli at 100 Hz, 200 ms apart), performed at two-third of the maximum fEPSP. Final LTP was determined over the last 10 min of the recording. We observed in both experiments a significant effect of genotype ($F_{3,103}=6.6$, $P<0.001$; Repeated measures ANOVA).

AS mice showed also a significant difference compare to wild-type animals in the group ($F_{3,102}=5.0$, $P<0.01$; Repeated measures ANOVA) (see drawing). Post hoc Bonferroni multiple comparisons analysis showed a significant improvement upon treatment with CX-8998 at both dosages (AS Vehicle vs CX-8998 30 mg/kg; P=0.01) (AS Vehicle vs CX-8998 60 mg/kg; P=0.02), and the MK-8998 treated AS mice were indistinguishable from the control ("wt") mice.

CX-8998 showed a significant improvement of LTP. This was observed with both dosages (30 and 60 mg/kg) and AS treated mice with CX-8998 were indistinguishable from wild-type mice.

The results of the experiment are shown in the drawing. The drawing shows that AS mice treated with vehicle had an LTP deficit compared to control mice, but administration of MK-8998 ("CX") at 30 mg/kg or at 60 mg/kg fully rescued the LTP deficit of the AS mice.

Example 2

Treatment of a Patient Suffering from Mild Cognitive Impairment

A patient has mild cognitive impairment which is characterized by the onset and evolution of cognitive impairments beyond those expected based on the age and education of the individual, but which are not significant enough to interfere with their daily activities. The patient is evaluated using one or more tests such as the Alzheimer disease (AD) Cooperative Study Clinician's Global Impression of Change for MCI (ADCS CGIC-MCI) such as the New York University (NYU) Paragraph Delayed Recall test, the modified AD Assessment Scale-cognitive subscale (ADAS-cog), and/or the Patient Global Assessment (PGA).

The patient is administered, alone or in combination with other therapies, a therapeutically effective amount of a T-type calcium channel antagonist provided herein (e.g., mibefradil, efonidipine, MK-8998 or the like). After a sufficient dosage of the T-type calcium channel antagonist has been administered for a period of time (e.g., after one dose or after a series of doses, e.g., over a period of 1-2 weeks), the patient's cognitive function is evaluated again. The patient shows an improvement in performance in the neuropsychological evaluation.

Other Embodiments

It is to be understood that while the invention has been described in conjunction with the detailed description thereof, the foregoing description is intended to illustrate and not limit the scope of the invention, which is defined by the scope of the appended claims. A number of embodiments of the invention have been described. Nevertheless, it will be understood that various modifications may be made without departing from the spirit and scope of the invention. Accordingly, other aspects, advantages, embodiments and modifications are within the scope of the following claims. It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

What is claimed is:

1. A method of treatment to improve memory and/or cognition in a subject in need thereof, comprising administering to the subject in need thereof a therapeutically effective amount of a T-type calcium channel antagonist, wherein the T-type calcium channel antagonist is MK-8998:

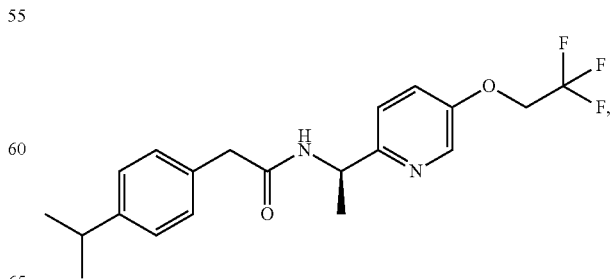

or a pharmaceutically acceptable salt thereof.

2. The method of claim 1, wherein the treatment improves cognition in the subject.

3. The method of claim 1, wherein the treatment improves memory in the subject.

4. The method of claim 1, wherein the treatment is for a cognitive disorder.

5. The method of claim 1, wherein the treatment is for a memory disorder.

6. The method of claim 1, wherein the treatment is for a condition selected from the group consisting of age-related cognitive impairment, agnosia, amnesia, amnestic disorder, amyotrophic lateral sclerosis, Asperger's syndrome, attention-deficit disorders, attention-deficit/hyperactivity disorders (ADHD), autism, cerebral amyloid angiopathy, cognitive dysfunction, cognitive impairment due to alcohol or drugs, delirium, dementia, AIDS-related dementia, alcoholic dementia, Alzheimer's disease, dementia associated with cerebral trauma, Creutzfeldt-Jakob disease and other prion-induced dementia, degenerative dementia, Huntington's disease, dementia associated with intracranial tumors, Lewy body disease, multi-infarct dementia, Parkinson's disease; Parkinsonian-ALS demential complex, Pick's disease, substance-induced persisting dementia, vascular dementia, Dravet Syndrome, head trauma, ischemia, learning disorders, learning impairment, memory impairment, memory loss, mental retardation, mild cognitive impairment, post-traumatic stress disorder, Prader-Willi Syndrome, progressive supranuclear palsy, stroke, traumatic brain injury, trisomy (including Trisomy 21 (Down Syndrome)), and Wernicke-Korsakoff's Syndrome.

7. The method of claim 1, wherein the treatment is for disorder that has an effect on cognitive and/or memory functions.

8. The method of claim 7, wherein the disorder that has an effect on cognitive and/or memory functions is selected from anxiety disorders, mood disorders and psychotic disorders.

9. The method of claim 1, further comprising administering to the subject an additional therapeutic agent.

10. The method of claim 9, wherein the additional therapeutic agent is an additional T-type calcium channel inhibitor.

* * * * *